(12) United States Patent  
Orup Jacobsen et al.

(10) Patent No.: US 6,517,864 B1  
(45) Date of Patent: Feb. 11, 2003

(54) TRANSDERMALLY ADMINISTERED TOLTERODINE AS ANTI-MUSCARINIC AGENT FOR THE TREATMENT OF OVERACTIVE BLADDER

(75) Inventors: Lene Orup Jacobsen, Gentofte (DK); Bo Kreilgard, Hillerod (DK); Ulla Hoeck, Hillerod (DK); Helle Kristensen, Slangerup (DK)

(73) Assignee: Pharmacia AB, Stockholm (SE)

( * ) Notice: Subject to any disclaimer, the term of this patent is extended or adjusted under 35 U.S.C. 154(b) by 0 days.

(21) Appl. No.: 09/763,654

(22) PCT Filed: Aug. 26, 1999

(86) PCT No.: PCT/SE99/01464  
§ 371 (c)(1),  
(2), (4) Date: Apr. 30, 2001

(87) PCT Pub. No.: WO00/12070  
PCT Pub. Date: Mar. 9, 2000

(30) Foreign Application Priority Data

Aug. 27, 1998 (SE) .............................................. 9802864

(51) Int. Cl.[7] .......................... A61F 13/00; A61F 13/02; A61K 9/70; A61L 15/16
(52) U.S. Cl. ...................... 424/449; 424/443; 424/447; 424/448
(58) Field of Search ................. 424/443, 447, 424/448, 449

(56) References Cited

U.S. PATENT DOCUMENTS 5,382,600 A    1/1995    Jonsson et al.

FOREIGN PATENT DOCUMENTS

| WO | 9323025 A1 | 11/1993 | |
|---|---|---|---|
| WO | 9803067 A1 | 1/1998 | |
| WO | 98/03067 | * 1/1998 | .......... A01N/33/18 |

OTHER PUBLICATIONS

Nilvebrant, L. Tolterodine—A New Bladder Selective Anti-muscarinic Agent. Eur. J. Pharmacol. 1977, vol. 327, pp. 195–207.*

* cited by examiner

Primary Examiner—Thurman K. Page  
Assistant Examiner—Humera N. Sheikh  
(74) Attorney, Agent, or Firm—Birch, Stewart, Kolasch & Birch, LLP

(57) ABSTRACT

Device for transdermal administration of tolterodine, optionally encompassing salts, prodrugs and metabolites thereof, optionally together with pharmaceutically acceptable carrier(s) to a human being or an animal in order to achieve an effect against overactive bladder. Use of a compound having an effect against overactive bladder comprising tolterodine, optionally encompassing salts, prodrugs and metabolites thereof, and optionally together with pharmaceutically acceptable carrier(s), for the manufacture of a composition to be administered transdermally for achieving an effect against overactive bladder. Method for achieving an effect against overactive bladder in a living body by transdermal administration of a compound comprising tolterodine, optionally encompassing salts, prodrugs and metabolites thereof, and optionally together with pharmaceutically acceptable carrier(s).

36 Claims, 32 Drawing Sheets

Matrix

Multi-laminate

Reservoir

Drug-in-adhesive

Backing    Membrane    Liner / skin    Adhesive    Drug

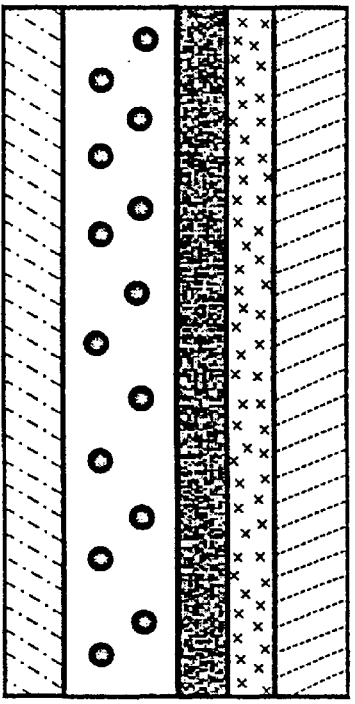
Fig. 1 B Multi-laminate
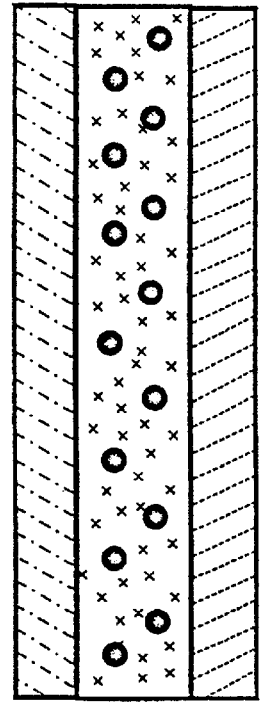
Fig. 1 D Drug-in-adhesive
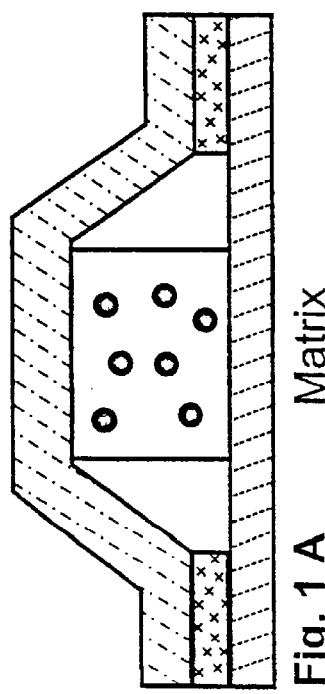
Fig. 1 A Matrix
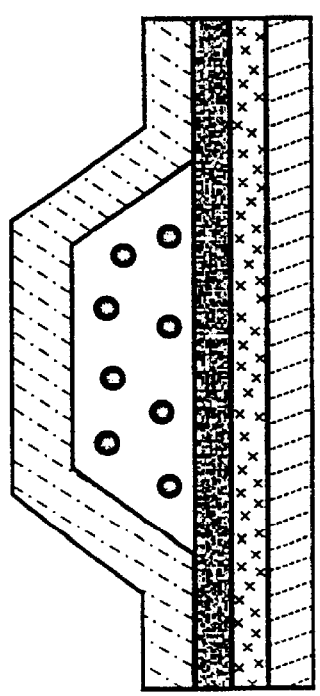
Fig. 1 C Reservoir
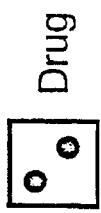
Drug
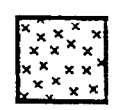
Adhesive
Liner / skin
Membrane
Backing

TRANSDERMALLY ADMINISTERED TOLTERODINE AS ANTI-MUSCARINIC AGENT FOR THE TREATMENT OF OVERACTIVE BLADDER

This application is the national phase under 35 U.S.C. § 371 of PCT International Application No. PCT/SE99/01464 which has an International filing date of Aug. 26, 1999, which designated the United States of America.

FIELD OF INVENTION

This invention relates to a device for transdermal administration of tolterodine, optionally encompassing salts, prodrugs and metabolites thereof, to the use of tolterodine, optionally encompassing salts, prodrugs and metabolites thereof, for the manufacturing of a medicament to be administered transdermally for achieving an effect against overactive bladder, and to methods of treating overactive bladder by transdermal administration of tolterodine, optionally encompassing salts, prodrugs and metabolites thereof.

BACKGROUND

Tolterodine is an effective and safe compound for treatment of overactive bladder. The synthesis of tolterodine and its utility for the treatment of overactive bladder is disclosed in U.S. Pat. No. 5,382,600 (Pharmacia & Upjohn AB). An optimal efficacy/side effect profile is obtained at an oral dosage of 1 or 2 mg twice daily. The high potency (and thereby low clinically effective serum concentrations) and the relatively short half-life (about 2 hours in the majority of the population, i.e. in extensive metabolisers, EMs) makes tolterodine a possible candidate for a patch formulation. Further properties supporting the feasibility of the patch principle are that the overactive bladder is a syndrome that might benefit of a flat serum concentration profile and that antimuscarinic compounds are not known to cause tolerance.

Tolterodine has a molecular weight of 325.0 and 475.6 as the tartrate salt. The enantiomeric purity is >99%. The $pK_a$ value is 9.87 and the solubility in water is about 11 mg/ml (room temperature). The partition coefficient (Log P) between n-octanol and phosphate buffer at pH 7.32 is 1.83.

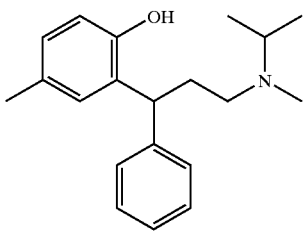

Tolterodine PNU-200583
N,N-dilso-propyl-3'-(2-hydroxy-5-methylphenyl)-3-phenylpropanamine.

The major metabolic pathway for the metabolism of tolterodine is mediated by cytochrome P450 2D6 leading to the formation of DD 01, (R)-N,N-diisopropyl-3-(2-hydroxy-5-hydroxymethylphenyl)-3-phenylpropanamine. DD 01 metabolite (also denoted 5-HM) has a similar pharmacological profile as tolterodine—see Nilvebrant L, Gillberg P-G, Sparf B. "Antimuscarinic potency and bladder selectivity of PNU-200577, a major metabolite of tolterodine." Pharmacol. Toxicol. (1997) 81: 195–207. For the similarity to tolterodine in pharmacological profile, see Brynne N, Dalen P, Alvan G, Bertilsson L and Gabrielsson J, Clin Pharmacol Ther 1998 (63): 529–39. A minor proportion of the population (the poor metabolisers, PMs) is devoid of the 2D6 isoenzyme and these subjects will show higher tolterodine concentrations but not measurable DD 01 levels.

The differences in tolterodine pharmacokinetic profile in EMs and PMs are not reflected in the clinical response, since the exposure to the sum of unbound tolterodine and DD 01 is similar in the two groups. The same oral dosage regimen can therefore be applied irrespective of phenotype. The transdermal concept is based on the same premise.

The present invention encompasses transdermal administration of tolterodine as R-isomer, S-isomer or as a racemic mixture.

PRIOR ART

Above-mentioned U.S. Pat. No. 5,382,600 does not disclose transdermal administration of tolterodine.

WO 98/03067 discloses the S-isomer of tolterodine. It claims transdermal administration of said S-isomer for treating urinary voiding disorders. It explicitly excludes transdermal administration of the R-isomer or of a racemic mixture. Anyhow WO 98/03067 only shows utility of the oral dosage form of said S-isomer. The transdermal administration thereof is just suggested, as are the parenteral, vaginal and aerosol routes, without any showing of utility.

WO 93/23025 and WO 96/23492 disclose transdermal administration of oxobutynin and of (S)-oxybutynin or (S)-desethyloxobutynin respectively for treating neurogenic bladder disorders. It should be noted that according to WO 93/23025 an enhancer is required in order to administer oxobutynin transdermally. Oxobutynin has a chemical structure being totally different from the one of tolterodine. WO 95/10270 discloses transdermal administration of S-terodiline for treating urinary incontinence. WO 96/27375 discloses transdermal administration of dextromethorphan or dextrorphan for treating urinary incontinence. WO 97/25984 discloses transdermal administration of a nitric oxide synthase substrate for treating urinary incontinence symptoms. WO 98/00141 discloses transdermal administration of enantiomerically enriched (S)-trihexyphenidyl for treating urinary incontinence. Anyhow none of the above substances have any similarities with tolterodine.

Hence the present invention, as further described below, is both new and inventive over prior art.

OBJECTS OF THE INVENTION

A transdermal formulation with tolterodine as active ingredient will provide an alternative to the tablet formulation for the oral route. The possibility exists that due to the more constant serum concentrations during a dosage interval, side effects in comparison to immediate release tablets, may be further reduced, while clinical efficacy is maintained.

The transdermal delivery route avoids the risk for dose dumping with extended release oral forms of administration. Moreover, patient compliance will be increased as
- elderly people and children may have difficulties in swallowing oral dosage forms
- patients can visually observe that they are taking their medication (contrary to not remembering whether you swallowed your tablet)
- once-a-day administration is possible
- several-days administration is possible with one patch.

Overall, these effects increase convenience and compliance for patients.

Accordingly, a first object of the present invention is to provide a device for transdermal administration of tolterodine, optionally encompassing salts, prodrugs and metabolites thereof, for achieving an effect against overactive bladder (encompassing detrusor instability, detrusor hyperreflexia, frequency, urgency and urge incontinence). The administration can be to a human being or to an animal. The administration may be performed without the use of an enhancer.

A second object of the invention is to provide use of a compound having an effect against overactive bladder, comprising tolterodine for the manufacture of a composition to be administered transdermally for treating overactive bladder or symptoms associated with this condition: i.e. urgency, frequency, nocturia and urge incontinence.

A third object of the invention is to provide a method of treating diseases, in humans or animals, which are treatable with antinuscarinic agents, by administering tolterodine transdermally.

Other objects of the invention will become apparent to one skilled in the art, and still other objects will become apparent hereinafter.

SUMMARY OF THE INVENTION

The present invention relates to transdermal administration of tolterodine, optionally encompassing salts, prodrugs and metabolites thereof for achieving an effect against overactive bladder. This effect is primarily achieved through the systemic effect of tolterodine. Anyhow other actions are not excluded.

BRIEF DESCRIPTION OF THE DRAWINGS AND THE TABLES

FIGS. 1A–1D are schematic drawings of different types of devices for transdermal delivery of drugs.

Figure 2:
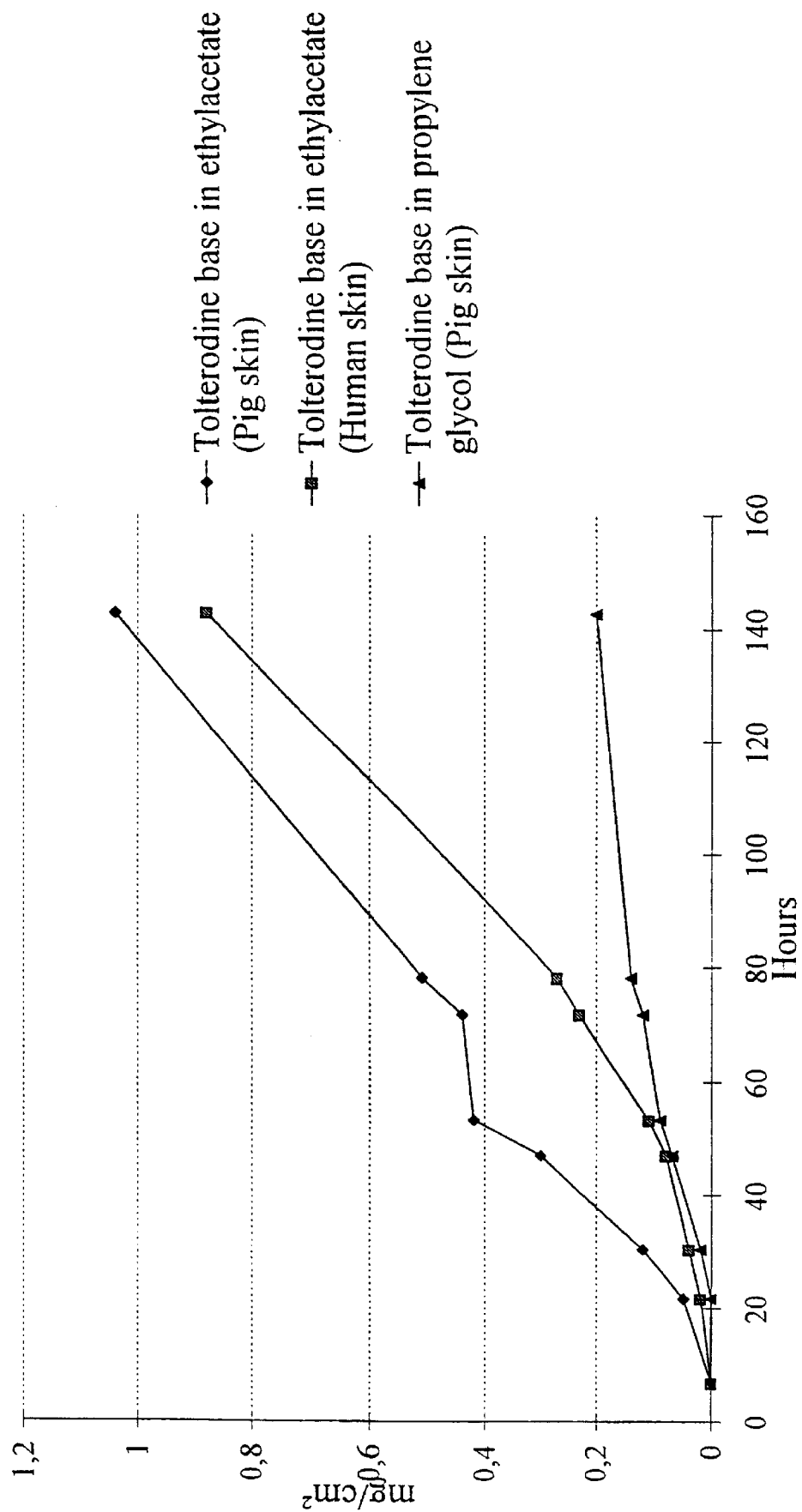
FIG. 2 is a diagram showing in vitro skin permeation of tolterodine base from different solvents according to Example 1.

Table 1 is an overview showing different factors influence on the rate control ability of a transdermal device.

Table 2 is an overview showing different tolterodine base formulations according to Example 5 and 6.

Table 3 is an overview showing different transdermal formulations with tolterodine base according to Example 9.

Table 4 is an overview showing different transdermal formulations with tolterodine base according to Example 12.

Table 5 is an overview showing different transdermal formulations with tolterodine base according to Example 14 and 15.

Table 6 is an overview showing stability data from different transdermal formulations with tolterodine base according to Example 18.

DETAILED DESCRIPTION OF THE INVENTION

Transdermal delivery of drugs can be achieved from topical products such as ointments or cremes or from transdermal devices. The present invention relates to administration via transdermal devices, which usually are called transdermal patches.

Devices usable as transdermal patches can be categorized in many different ways. A comprehensive categorization of transdermal devices is found in Wick S. Developing A Drug-In-Adhesive Design For Transdermal Drug Delivery. Adhe Age 1995; 38: 18–24.

Wick essentially divides transdermal devices into the below four main groups:

the reservoir type, in which the drug is placed in a liquid or a gel and delivered across a rate-moderating membrane to the skin;

the matrix type, in which the drug is placed within a non-adhesive polymeric material, typically a hydrogel or soft polymer;

the drug-in-adhesive type, in which the drug is placed within an adhesive polymer;

the multi-laminate type, which is similar to the drug-in-adhesive design but which incorporates an additional layer of pressure sensitive adhesive to cover the entire device and affix it to the skin. A membrane can also be incorporated into this multi-laminate type as shown in FIG. 1B.

The above four main types of transdermal devices are schematically illustrated in FIGS. 1A–1D.

A fifth important type, not mentioned by Wick, is the iontophoretic type, which is the predominant mechanism for electrically assisted transdermal delivery. When using the iontophoretic type, an electrical potential gradient is used for transferring the drug through the skin—see further e.g. Singh P et al. Iontophoresis in Drug Delivery: Basic Principles and Applications. Crit Rev Ther Drug Carrier Syst 1994; 11: 161–213.

Besides this, electroporation, electroosmosis, electroincorporation and et injection can be used.

Electroporation is the creation of transient aqueous pores in lipid bilayer membranes by the application of a short (msec) electric pulse (Prausnitz M R et al. Proc Int Symp Control. Rel Biact Mater 1993; 20: 95–96). By using electroporation the skin permeability will be altered such that resistance to drug transport is reduced. Electroporation has been employed in transdermal drug delivery by coupling it with iontophoresis (Bommannan D et al. Pharm Res 1994; 11: 1809–1814, Prausnitz M R et al. Proc Na Acad Sci USA 1993; 90: 10504–10508, and Riviere J E et al. J Controlled Release 1995; 36: 299–233). In these cases, a short (few milliseconds) pulse of high voltage alters the skin permeability such that subsequent iontophoresis is facilitated.

With electroosmosis the electric field creates a convective flow of water which allows hydrophilic compounds to be transported. Closely related to electroporation is electroincorporation but here particles (microspheres, liposomes) are placed on the surface of the skin and subsequent high voltage electrical pulses are employed (Riviere J E and Heit M C. Pharm Res 1997; 14: 687–697).

Jet injection can be used both for powders and liquids (Muddle A G et al. Proc lnt Symp Control. Rel Biact Mater 1997; 24: 713–714, and Seyam R M et al. Urology 1997, 50: 994–998. By using jet injection a drug can be administered by a no-needle painless injection.

The above split-up into groups is not very strict as variations and combinations of each may be envisaged. So may a multi-laminate type device encompass a device with many layers in a sandwich construction, such as the drug in one layer, excipients such as enhancers in a further layer, a membrane in another layer and an adhesive in still another layer. Or it could be composed of several drug,-in-adhesive layers or combinations of the above layers.

The liquid or gel used in the above reservoir type device could be hydrophilic or lipophilic, such as water, alcohols, mineral oils, silicone fluids, various copolymers, such as ethylene vinyl acetate, vinyl acetate or polyvinyl alcohol/polyvinyl pyrrolidone. The reservoir may also include dyes, inert fillers, diluents, antioxidants, antiirritants, antisensitizers, permeation enhancers, stabilizers, solubilizing agents and other pharmacologically inactive pharmaceutical agents being well known in the art.

The adhesives used are generally of three types, being the rubber type, encompassing inter alia polyisobutylenes, the acrylate type and the silicone type. The adhesives may be chemically modified, and may have a wide range of molecular weights. To the adhesive could be added several types of excipients such as fillers, stabilizers, plasticizers, buffering agents, permeation enhancers, permeation retarders, antiirritants, antisensitizers, solubilizing agents and other pharmaceutical ingredients being well known in the art.

Polymer films that may be used for making the rate-moderating membrane include, without limitation, those comprising low- and high-density polyethylene, ethyl vinyl acetate copolymers and other suitable polymers.

The backing layer serves the purposes of preventing passage of the drug and/or environmental moisture through the outer surface of the patch, and also for providing support for the system, where needed. Further the backing layer can provide occlusion, and thus increasing the rate of delivery of the drug into the skin. The backing layer may be chosen so that the end product is appealing to the users, whether children, adults, elderly people or other customer groups. The backing layer is impermeable to the passage of tolterodine or inactive ingredients being present in the formulation and can be flexible or nonflexible. Suitable materials include, without limitation, polyester, polyethylene terephthalate, some type of nylon, polypropylene, metallized polyester films, polyvinylidene chloride and aluminium foil.

The release liner can be made of the same materials as the backing layer.

As will be clear further below the invention according to the present application encompasses administration of tolterodine via all hitherto known types of devices for transdermal administration. Mainly the above categorization will be adhered to in this application. Anyhow this does not exclude that transdermal devices which might fit better according to some other categorization also are included in the present invention.

It is well known in the art that the properties of the skin as such influence the permeation of the drug through the skin into the systemic circulation. It could thus be said that the skin controls the drug permeation rate. Anyhow as the skin as such is no part of the present invention the behaviour of the skin in connection with transdermal drug delivery will not be discussed in detail. It is also well accepted in the art that when rate-controlling properties are attributed to a transdermal device is meant properties associated with the release rate from the device as such. It is also evident that when a transdermal device is designed to exhibit a certain release performance the properties of the skin need be taken into consideration during the design process.

Hydrogels (used for the matrix type and reservoir transdermal systems) are materials, which swell when placed in excess water. They are able to swell rapidly and retain large amount of water in their swollen structure. The materials do not dissolve in water and maintain three-dimensional networks. Hydrogels are usually made of hydrophilic polymer molecules which are crosslinked either by chemical bonds or other cohesion forces such as ionic interaction, hydrogen bonding or hydrophobic interaction. Hydrogels are elastic solids in the sense that there exist remembered reference configurations to which the system returns even after being deformed for a very long time (Park K et al. Biodegradable Hydrogels for Drug Delivery. Technomic Publishing Co., Inc. 1993). Examples of hydrogels are polyvinylpyrrolidone and cellulose hydrogels such as methylcellulose, hydroxyethylcellulose, hydroxyethylmethylcellulose, carboxymethylcellulose, ethylcellulose, hydroxypropylmethylcellulose, hydroxypropylcellulose and microcrystalline cellulose (colloidal). Other examples are: Guar gum, gum arabic, agar, tragacanth, carrageenan, xanthan gum, algin, carbomer, dextran and chitin.

Also it could be possible to manufacture a polymer-system with no foils (backing membrane and release liner)

consisting of 1, 2 or more polymers in a solvent and added drug and eg. plasticizers and enhancers. The polymers could be a blend of hydrophilic and hydrophobic species. This product should be applied to the skin using an appropriate device where the solvent evaporates and leaving a thin invisible film. This type of systems can also be of a multi-layer type where the drug could be incorporated in different layers of polymers with different release characteristics and/or alternative layers without drug that could act as a rate limiting membrane. The outer layer is most preferable hydrophobic to obtain occlusion.

The rate control ability is often a very important feature for a transdermal device in order to deliver the correct amount of drug to the patient at the correct time. Thereby maximum efficacy is achieved while side effects are minimized. Many factors influence the rate control ability of a transdermal device. In the below Table 1 the most important such factors are listed and their influence in the respective device type is marked. A plus sign indicates that the influence is strong. The absence of a plus sign does not exclude that the corresponding factor has at least some influence.

TABLE 1

| | Type of device | | | |
|---|---|---|---|---|
| Factor | Reservoir | Matrix | Drug-in-adhesive | Multi-laminate |
| Polymer type(s) | + | + | + | + |
| Modification of the polymer(s) | | + | + | + |
| Activity, i.e. concentration, of drug e.g. supersaturation | + | + | + | + |
| Additives in polymer(s) | | | | |
| Enhancer(s) | + | + | + | + |
| Cyclodextrine(s) | + | + | + | + |
| Retarder(s) | + | + | + | + |
| pH-adjustment | + | + | + | + |
| Solubilizer(s) | + | + | + | + |
| Emulsifier(s) | + | + | + | + |
| Membrane(s) | | | | |
| Hydrophilic | + | | | |
| Lipophilic | + | | | |
| Thickness | + | | | |
| Pore size | + | | | |
| Density | + | | | |
| Chemical stabilizer(s) | + | + | + | + |

Taking into account the convenience of wearing a patch as well as ease of manufacturing, the drug-in-adhesive and the reservoir type device are presently considered to be the best modes for carrying out the present transdermal delivery of tolterodine.

It may also be desired to include, at least in some device types, one or more transdermal permeation enhancing substance(s) in order to increase the amount of tolterodine which may permeate the skin and reach the systemic circulation, or in order to reduce the size of the patch. Enhancers suitable in the present invention may be categorized in the below groups, although enhancers not belonging to any of these groups are not excluded.

alcohols, such as short chain alcohols, e.g. ethanol and the like, long chain fatty alcohols, e.g. lauryl alcohols, and the like, and polyalcohols, e.g. propylene glycol, glycerin and the like;

amides, such as amides with long aliphatic chains, or aromatic amides like N,N-diethyl-m-toluamide;

amino acids;

azone and azone-like compounds;

essential oils, i.e. essential oils or constituents thereof, such as 1-carvone, 1-menthone-menthol, and the like;

fatty acids and fatty acid esters, such as oleic acid, lauric acid and the like, further esters of fatty acids, such as isopropyl myristate, and various esters of lauric acid and of oleic acid and the like;

macrocyclic compounds, such as cyclopentadecanone and cyclodextrins;

phospholipid and phosphate compounds, such as phospholipids;

2-pyrrolidone compounds; and miscellaneous compounds, like sulphoxides, such as dimethyl sulphoxides, and fatty acid ethers, such as Laureth-9 and polyoxylaurylether.

Combinations of enhancers from different groups in the above categorization may prove very useful and efficient.

For overview of enhancers, see further e.g. Santus G C et al. Transdermal enhancer patent literature. J Control Release 1993; 25: 1–20, and Smith E W et al. Percutaneous penetration enhancers. CRC Press Inc. 1995.

DETAILED DESCRIPTION OF THE INVENTION

The following, examples are intended to illustrate but not to limit the scope of the invention, although the embodiments named are of particular interest for our intended purposes.

Materials and apparatus used in the examples

Materials

Drug

Tolterodine base, tolterodine L-tartrate and DD 01 were supplied by Pharmacia & Upjohn (Uppsala, Sweden).

Polymers

Eudragit RL 30D, Eudragit RL 100 and Robi 2787F were supplied by Röhm GmbH Chenuische Fabrik, Polyvidone 90 was supplied by BASF, MA-24 were from Adhesives Research, Inc., silicone adhesive PSA-9839 were from NuSil Technology and Durotak387-2052, 387-2054, 387-2287, 387-2516, 387-2353, 387-2825, 387-2620, 87-2070 and 87-2852 were supplied by National Starch & Chemical.

Foils

The siliconized polyester release liners (S 2016 and FL2000-696029/3) were obtained from Rexam Release, the fluoropolymer coated release liner (Scotchpak 1022), the backins membranes (Scotchpak 1012 and 1109) and CoTran membranes (with 9% and 19% vinyl acetate (VA) respectively) were all obtained from 3M Corp. The nonocclusive backing membrane ("Emflon 11" 0.2 mm PVDF membrane) were from Pall Specialty Materials.

Other materials

Sodium Hydroxide, disodium hydrogen phosphate, Tween 80, ethyl acetate and propylene glycol were supplied by Merck. Triethylacetate were supplied by Fluka, methyl laurate (Estol 1507) by Unichema and ethanol 99,9% by Danisco Distillers.

Patch formulation studies

The patches were prepared by either dissolving the tolterodine base directly into the polymers or by dissolving it in a solvent before adding to the polymer. Coating of the drug gel was performed using either:

1) a coating equipment (RK Print Coat Instr. LTD, Type KCC 202 control coater) or 2) a Laboratory Coater (Pagendarm, Type RAM 300).

After drying, an adhesive layer was laminated to some of the formulations resulting in either a drug-in-adhesive laminate (no extra adhesive layer) or a multi-laminate (with extra adhesive layer).

Reservoir formulation study

The tolterodine base was dissolved in ethanol and propylene glycol. Methyl laurate was added and the solution was thereafter filled in reservoir patches by use of a reservoir machine (A&D, GmbH, Type PF-80).

Quantitative HPLC-determination of tolterodine content

Method used for Example 3:

The content of tolterodine base in the patches were determined using a HPLC method. The system consisted of a Pharmacia LKB HPLC pump 2248, a Marathon-XT Autosampler, a Pharmacia LKB UV-visible detector 2141 and as data handling system was used Hewlett Packard Vectra VL2 PC with EZ-chrom software. The Nucleosil C18 column 5 µm 120×4 mm i.d. was from Phenomenex.

The mobile phase consisted of 0.1M phosphate buffer pH 2.5:acetonitrile (680:320, v/v). The flow rate was 1.0 ml/min., UV-detection was performed at 280 nm and the injection volume was 20 µl.

Method used for Examples 5. 6. 9. 12 14. 15. 19 and 37:

The content of tolterodine base in the patches were determined using a HPLC method. The system consisted of a Pharmacia LKB HPLC pump 2248, a Marathon-XT Autosampler, a Pharmacia LKB UV-visible detector 2141 and as data handling system was used Hewlett Packard Vectra VL2 PC with EZ-chrom software. The Nucleosil C18 column 5 µm 150×4.6 mm i.d. was from Phenomenex.

The mobile phase consisted of 0.05M phosphate buffer pH 2.5:acetonitrile (550:450, v/v). The flow rate was 1.0 ml/min., UV-detection was performed at 285 nm and the injection volume was 50 µl.

Method used for Example 25:

The content of DD 01 in the patches was determined using a HPLC method. The system consisted of a Pharmacia LKB HPLC pump 2248, a Marathon-XT Autosampler, a Pharmacia LKB UV-visible detector 2141 and as data handling system was used Hewlett Packard vectra VL2 PC with EZ-chrom software. The Nucleosil C18 coloumn 5 µm 150×4.6 mm was from Phenomenex.

The mobile phase consisted of 0.05M phosphate buffer pH 2.5:acetonitrile (600:400, v/v) with 1.0 g of octanesulphonic acid/1000 ml. The flow rate was 1.0 ml/min., UV-detection was performed at 280 nm and the injection volume was 50 µl.

In vitro dissolution studies

In vitro dissolution studies were performed according to USP 23, p. 1797 (Apparatus 5, paddle over disk method). The system consisted of a Pharma Test Type PTW S3C six-vessel dissolution apparatus. As dissolution medium was used 600 ml (500 ml for Example 4) of 0.05M phosphate buffer, pH 7.4 equilibrated to 32±0.5° C. Samples were removed periodically and measured by HPLC.

For Examples 30 and 38 the apparatus was modified by use of a convex screen (TDS-CR) to hold the transdermal systems in position during testing.

In vitro skin permeation studies

In vitro skin permeation results were obtained from studies on pig or human skin using Franz diffusion cells.

Full thickness pig and human skin (used in Example 1) or 765 µm skin (used in all other Examples) was used. The 765 µm skin was isolated by using a dermatome (Zimmer Electric Dermatome 8821, Zimmer Chirurgie).

The skin was mounted in the diffusion cells with an available diffusion area of 1.8 cm². The inner side of the skin was exposed to 12.1 ml receptor phase (0.05M phosphate buffer, pH 7.4) at 37±1° C. Samples were withdrawn periodically and measured by HPLC. Fluxes (>g/cm²/h) were obtained by linear regression of data at steady state.

EXAMPLES

Example 1

In vitro skin permeation studies from solutions of tolterodine base.

Solution 1

240 mg tolterodine base was dissolved in 20 ml propylene glycol

Solution 2

240 mg tolterodine base was dissolved in 20 ml ethyl acetate

In vitro skin permeation of tolterodine base from solution 1 and 2 respectively through full thickness pigskin was investigated using Franz diffusion cells. For tolterodine base in solution 2 also human full thickness skin was used. The cumulative amount of tolterodine base in the receptor solution versus time is shown in FIG. 2. An increase in the amount of tolterodine base is seen in the following order. Ethyl acetate>propylene glycol. The results show that it should be possible to adjust the flux through the skin by changing the solvent.

Example 2

In vitro permeation studies across synthetic membranes and dermatomed pig skin from solutions of tolterodine base, imitating the reservoir type transdermal device. Enhancer was added to one of the solutions.

Solution 3

0.5 g tolterodine base in 9.5 g 1% hydroxypropylcellulose (EPC)/ethanol.

Solution 4

0.5 g tolterodine base in 9.5 g 3% HPC/ethanol

Solution 5

0.5 g tolterodine base in 9.5 g methyl laurate:ethanol (1:9)

In vitro skin permeation of tolterodine base from the solutions 3, 4 and 5 across 2 different synthetic membranes was investigated using Franz diffusion cells. Membranes of the following types were used: CoTran 9702 (microporous polyethylene film) with 9% vinyl acetate (VA) and CoTran 9728 with 19% vinyl acetate. The solutions 3 and 4 were both applied on the surface of the two mentioned membranes while solution 5 only was applied on the surface of the CoTran 9702 membrane with 9% vinyl acetate. The membranes were placed on top of dermatomed pigskin. The inner sides of the pigskin were exposed to 12.1 ml receptor solution (0.05M phosphate pH 7.4 equilibrated to 37±1° C.).

Figure 3:
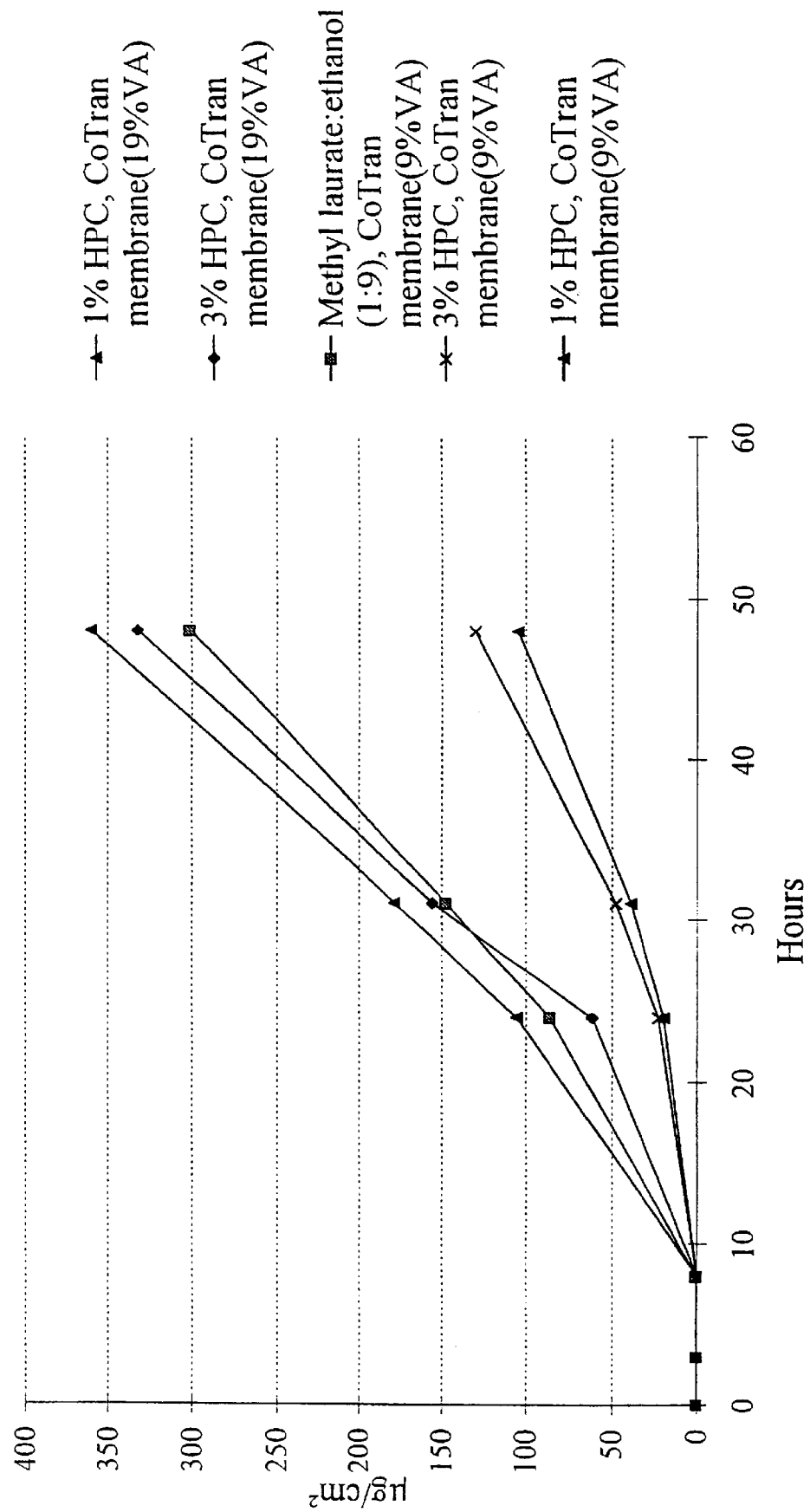
FIG. 3 is a diagram showing in vitro skin permeation of tolterodine base through different membranes according to Example 2.

The cumulative amount of tolterodine base in the receptor solution versus time is shown in FIG. 3. The fluxes were about 4 µg/cm²/h when using 1 or 3% HPC and 9% VA CoTran membrane, about 11 µg/cm²/h when using 1 or 3% HPC and 19% VA CoTran membrane and 9 µg/cm²/h when using enhancer and 9% VA CoTran membrane. The results show that it is possible to control the release rate of tolterodine base from a reservoir type device by changing the membrane. Also it was seen that when enhancer was added a higher flux was obtained.

Example 3

System 1 (drug-in-adhesive, acrylate)

Loading of different acrylates with tolterodine base 5 g tolterodine base was dissolved in 11 g ethanol and added to 20 g Durotak 387-2287. The drug gel was coated onto a backing membrane (Scotchpak 1012) by using the coating equipment. Wet layer thickness was 400 µm. The laminate was dried for 20 min. at RT and then for 30 min. at 40° C. A polyester release liner (S 2016) was laminated onto the dried drug gel. The sheet was cut into patches and stored at 2–8° C. until use (packed in Barex pouches). The concentration of tolterodine base in the patches was 2,5 mg/cm$^2$.

System 2 (multi-laminate, acrylate)

5 g tolterodine base was dissolved in 10 ml ethanol. A mix of 6,4 g Eudragit RL 100 and 6,4 g ethanol and a mix of 2,6 g Polyvidone 90 and 10,2 g ethanol was added the solution of tolterodine base in ethanol. At last 4 g propylene glycol was added. The drug gel was coated onto a backing membrane (Scotchpak 1109) by using the coating equipment. Wet layer thickness was 400 µm. The laminate was dried at 40° C. for 2 hours. An adhesive layer consisting of Plastoid E35H was coated onto a polyester film (S 2016) and dried at 80° C. for 10 min. The 2 layers were thereafter laminated. The sheet was cut into patches and stored at 2–8° C. until use (packed in Barex pouches). The concentration of tolterodine base in the patches was 2,0 mg/cm$^2$.

System 3 (multi-laminate, waterbased acrylate)

1 g tolterodine base was mixed with Tween 80 by heating to 60–70° C. 1,8 g triethylacetate and 1,3 g dem. water was added to the mix. The final mix was then added to 25 g Eudragit RL 30 D. At last 180 mg 1N NaOH was added. The drug gel was coated onto a backing membrane (Scotchpak 1109) by using the coating equipment. Wet layer thickness was 400 µm. The laminate was dried at 40° C. for 2 hours. An adhesive layer consisting of Plastoid E35H was coated onto a polyester film (S 2016) and dried at 80° C. for 10 min. The 2 layers were thereafter laminated. The sheet was cut into patches and stored at 2–8° C. until use (packed in Barex pouches). The concentration of tolterodine base in the patches was 0,5 mg/cm$^2$.

Example 4

Figure 4:
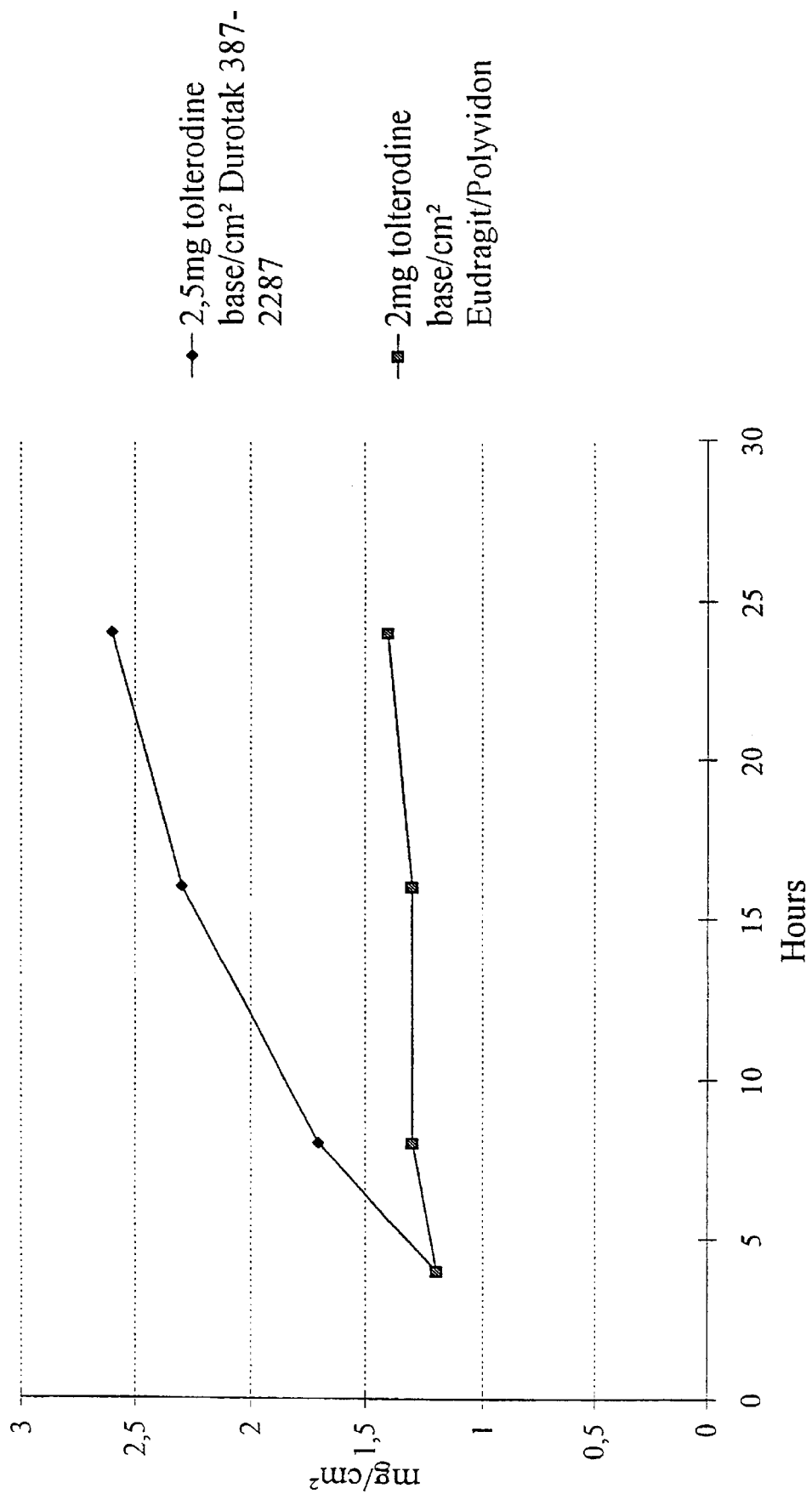
FIG. 4 is a diagram showing in vitro dissolution of tolterodine base from different transdermal systems according to Example 3.
Figure 5:
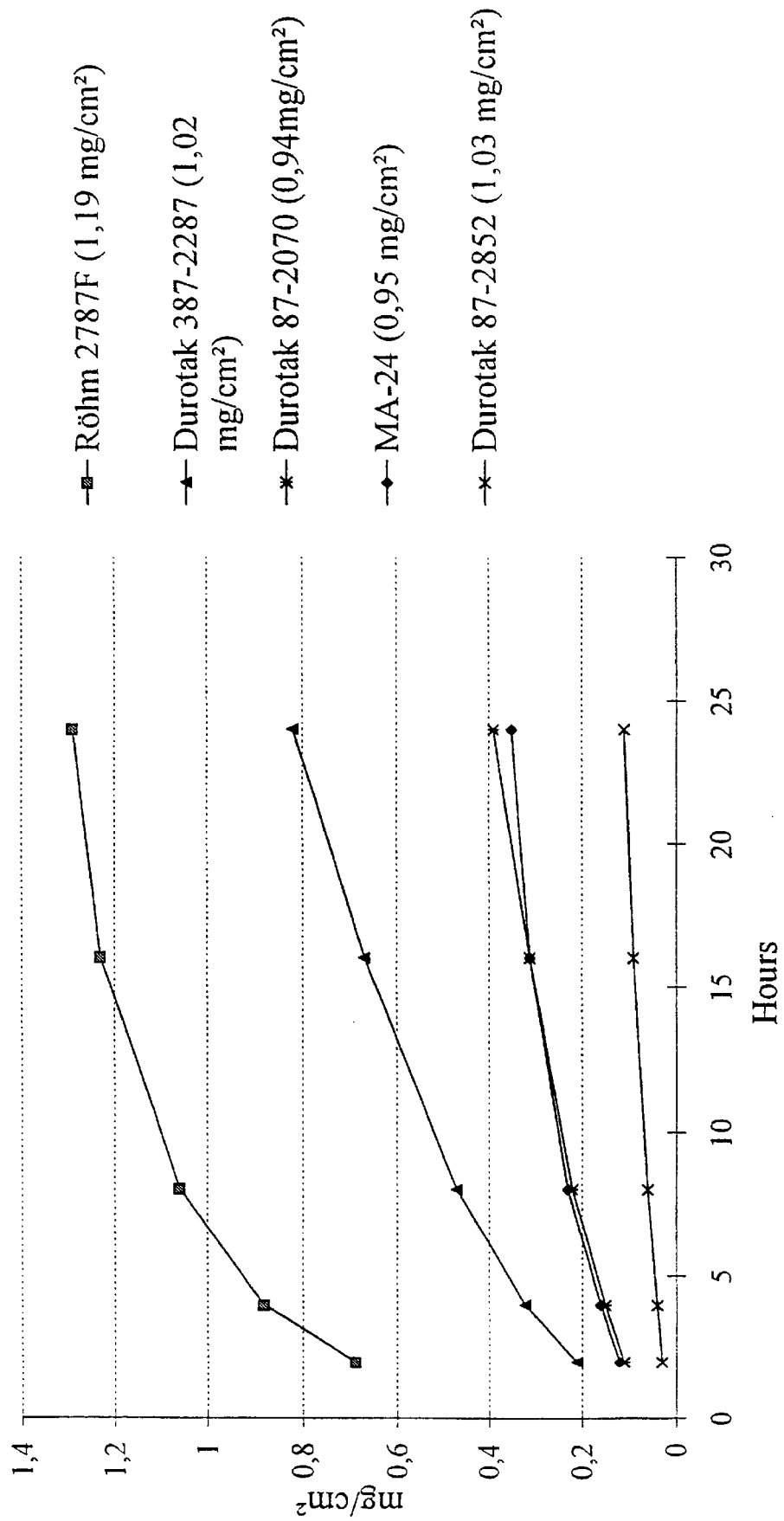
FIGS. 5, 6, 7, 8 and 9 are diagrams showing in vitro dissolution of tolterodine base from different transdermal systems according to Example 7.
Figure 6:
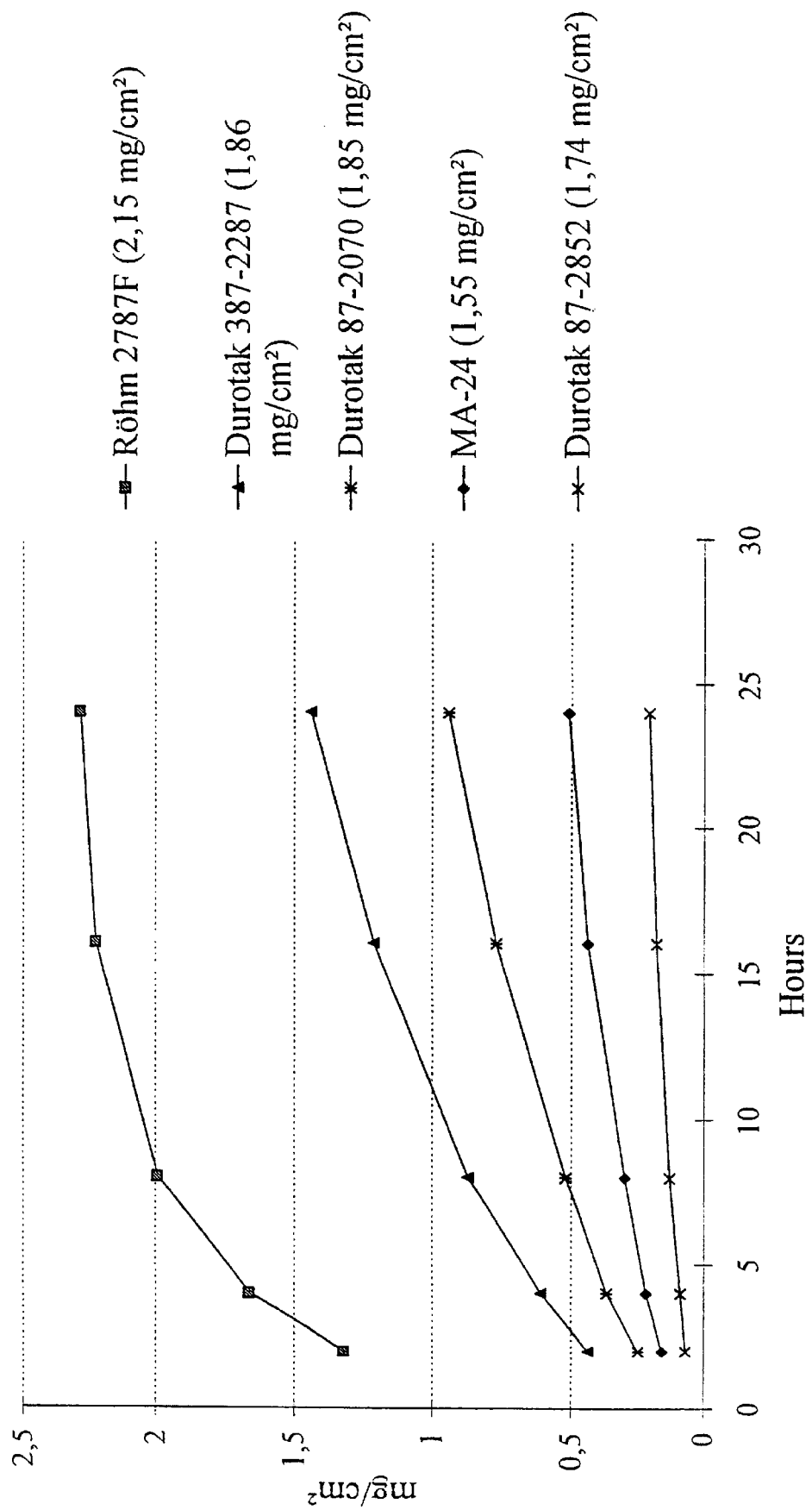
Figure 7:
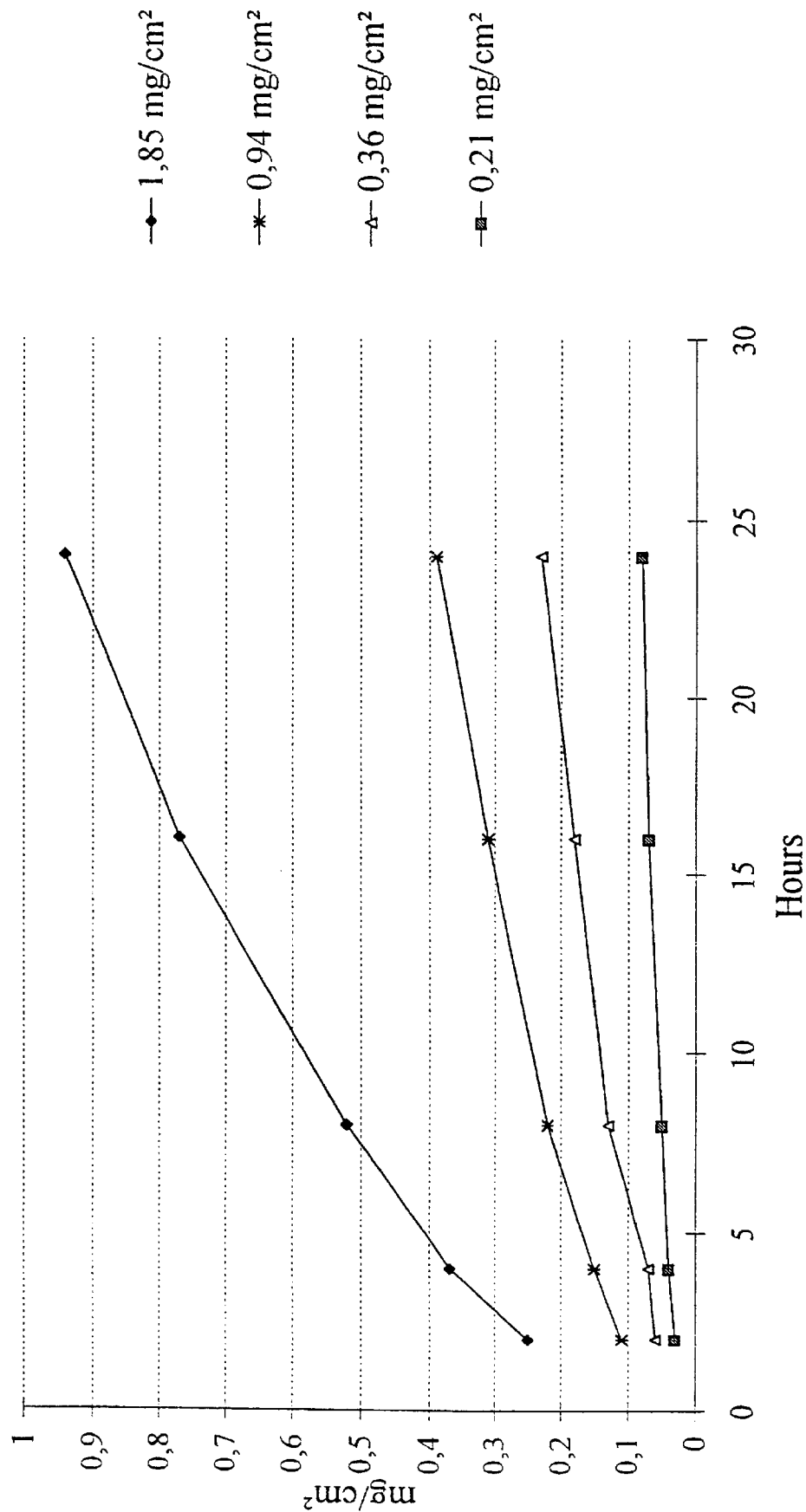
Figure 8:
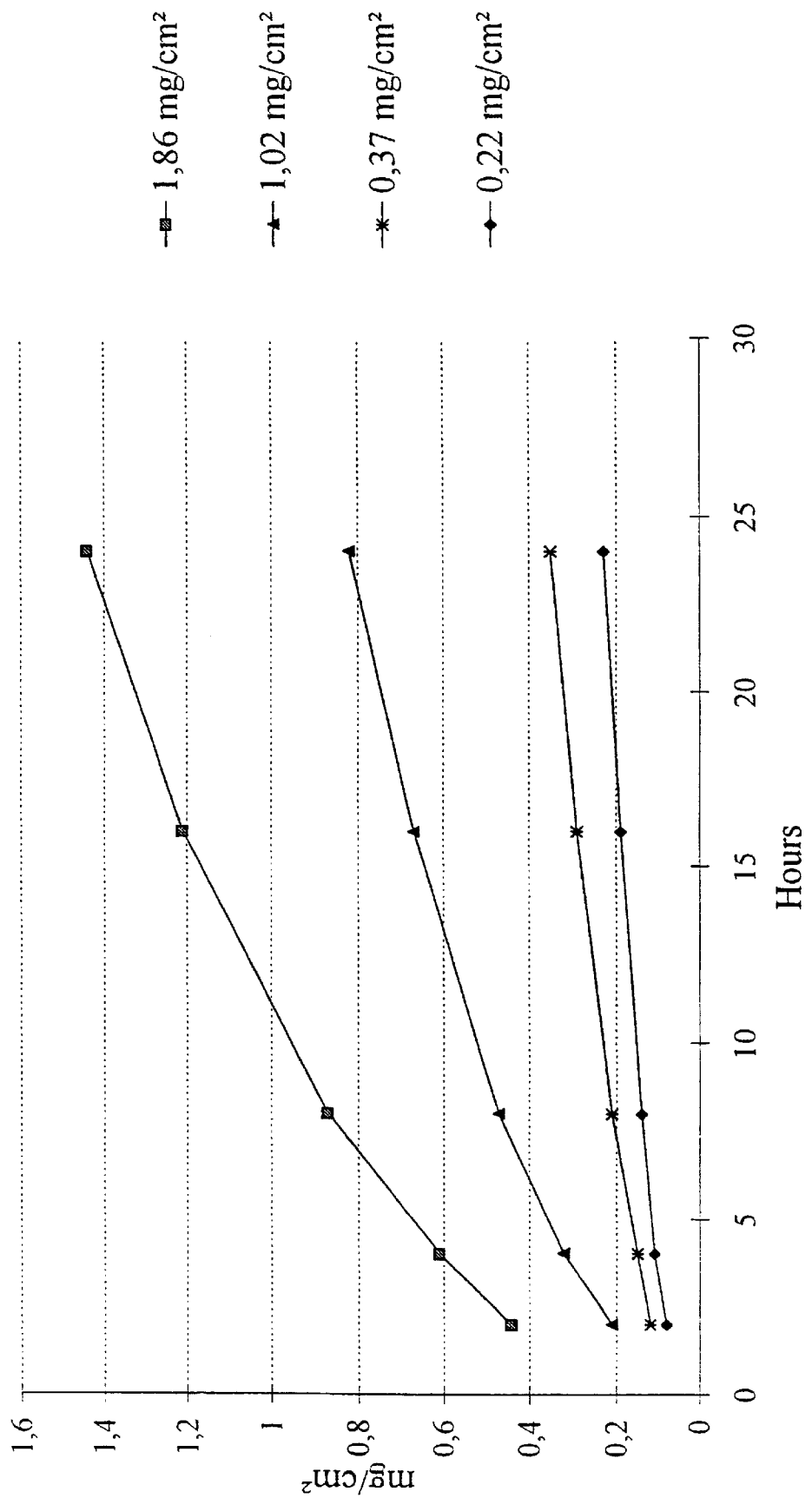
Figure 9:
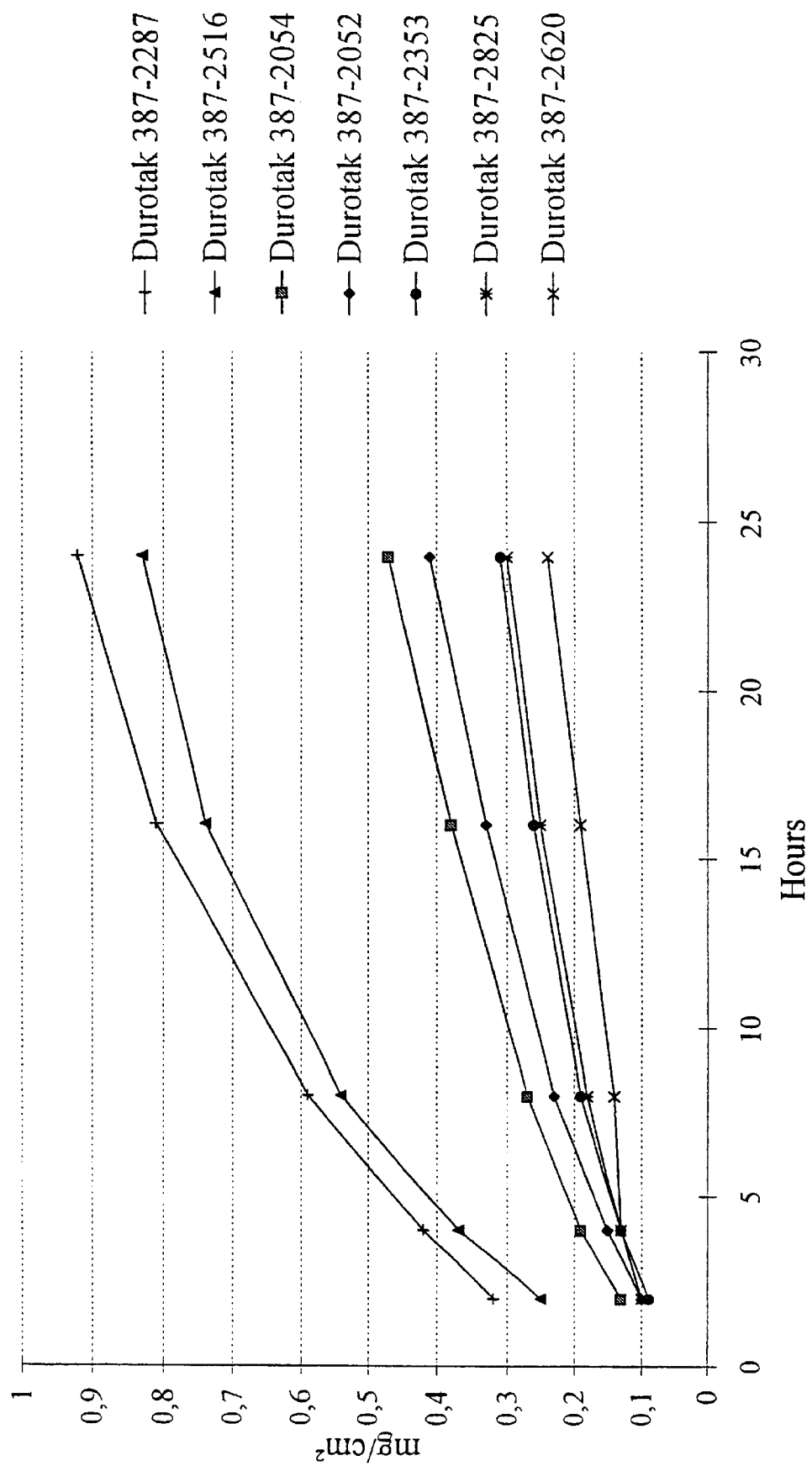
Figure 10:
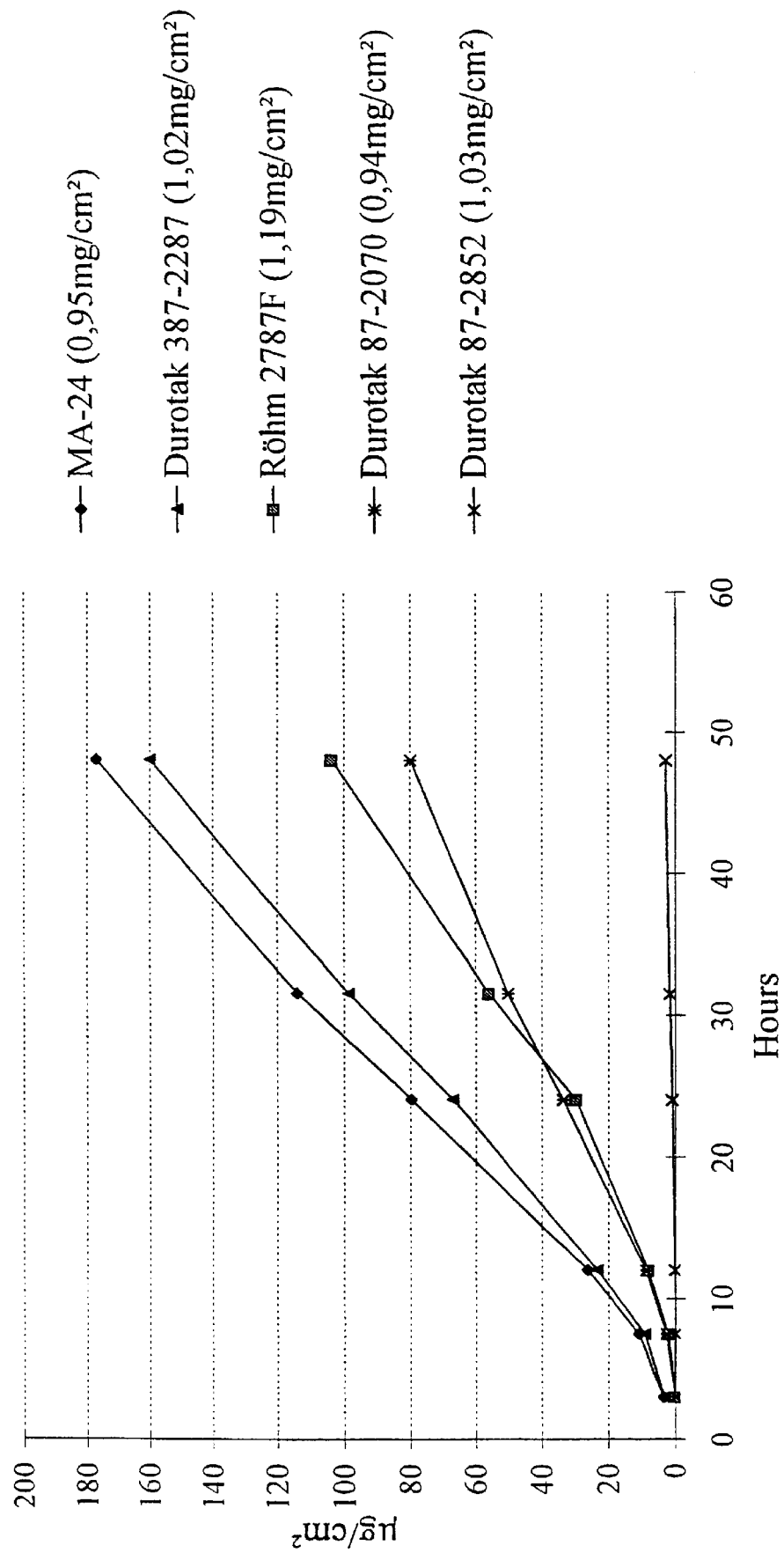
FIGS. 10, 11, 12, 13 and 14 are diagrams showing in vitro skin permeation of tolterodine base from different transdermal systems according to Example 8.
Figure 11:
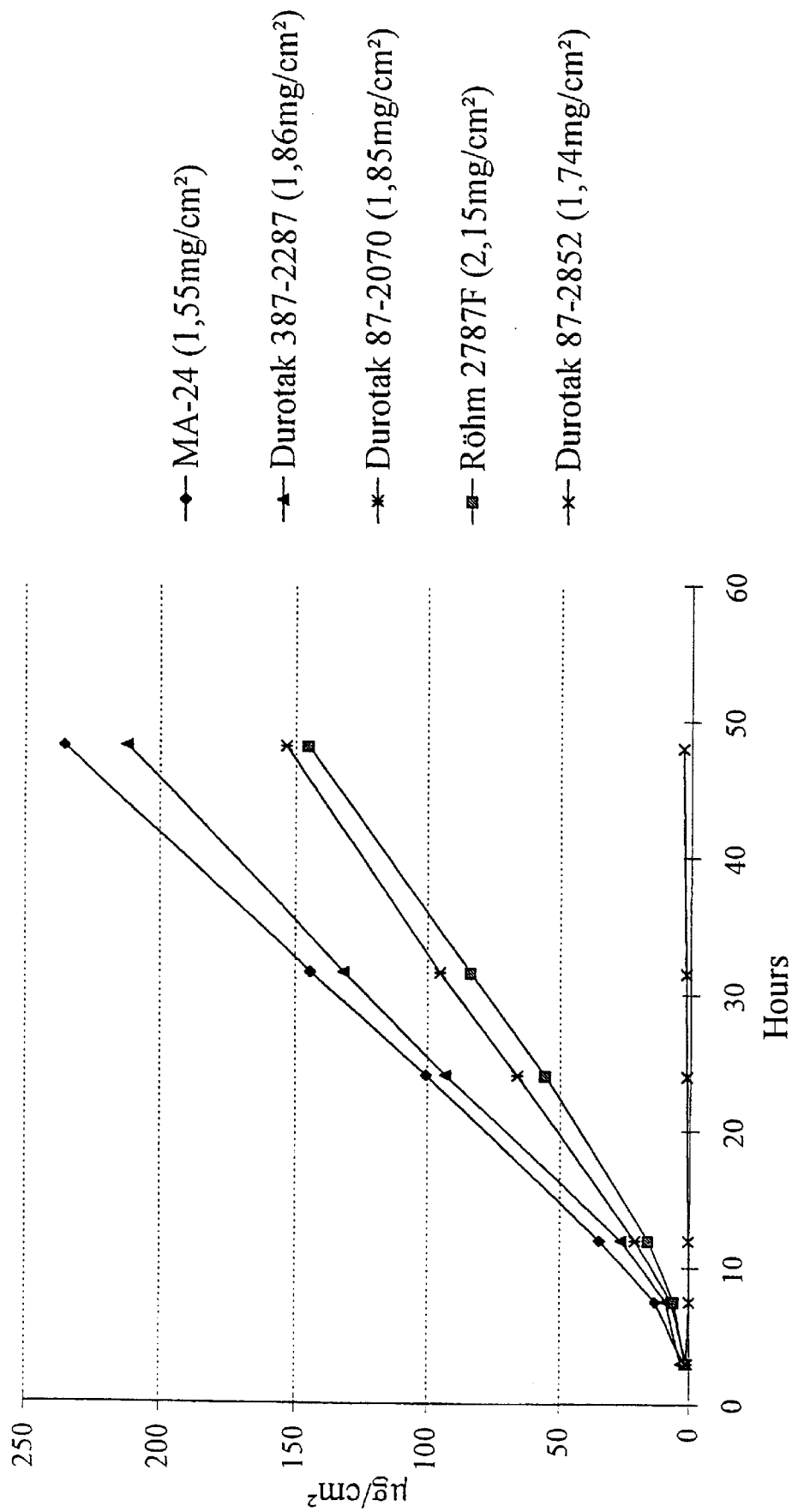
Figure 12:
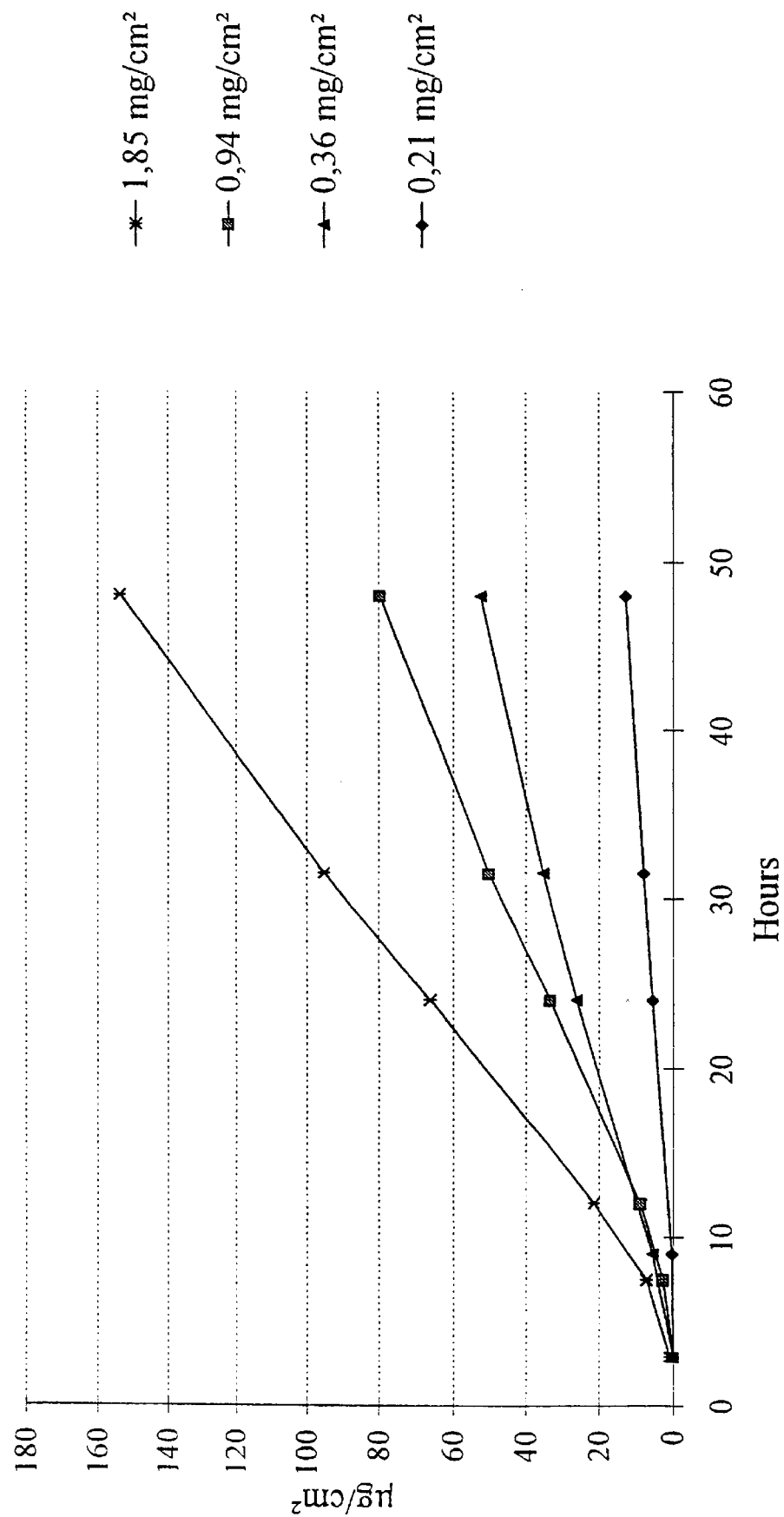
Figure 13:
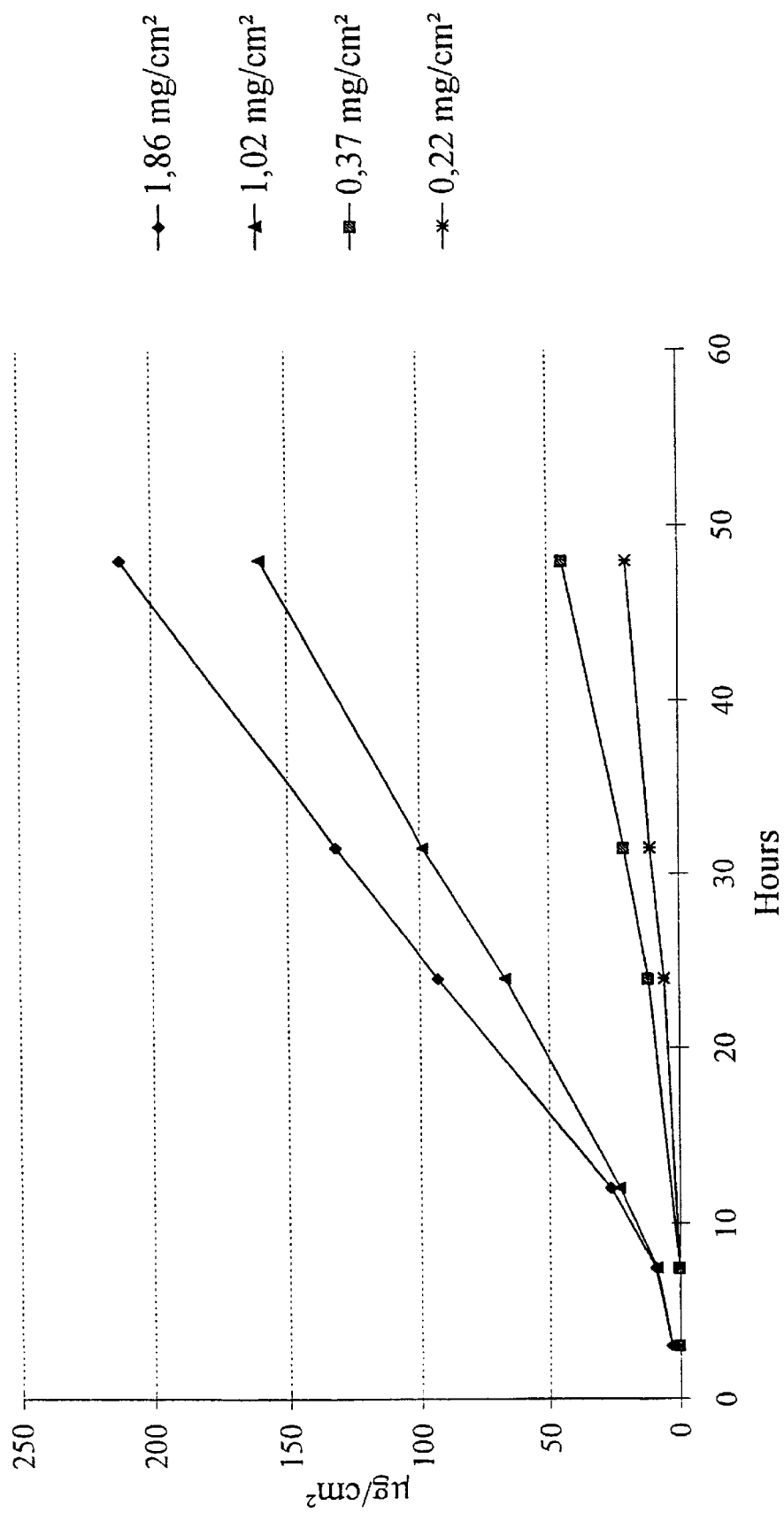
Figure 14:
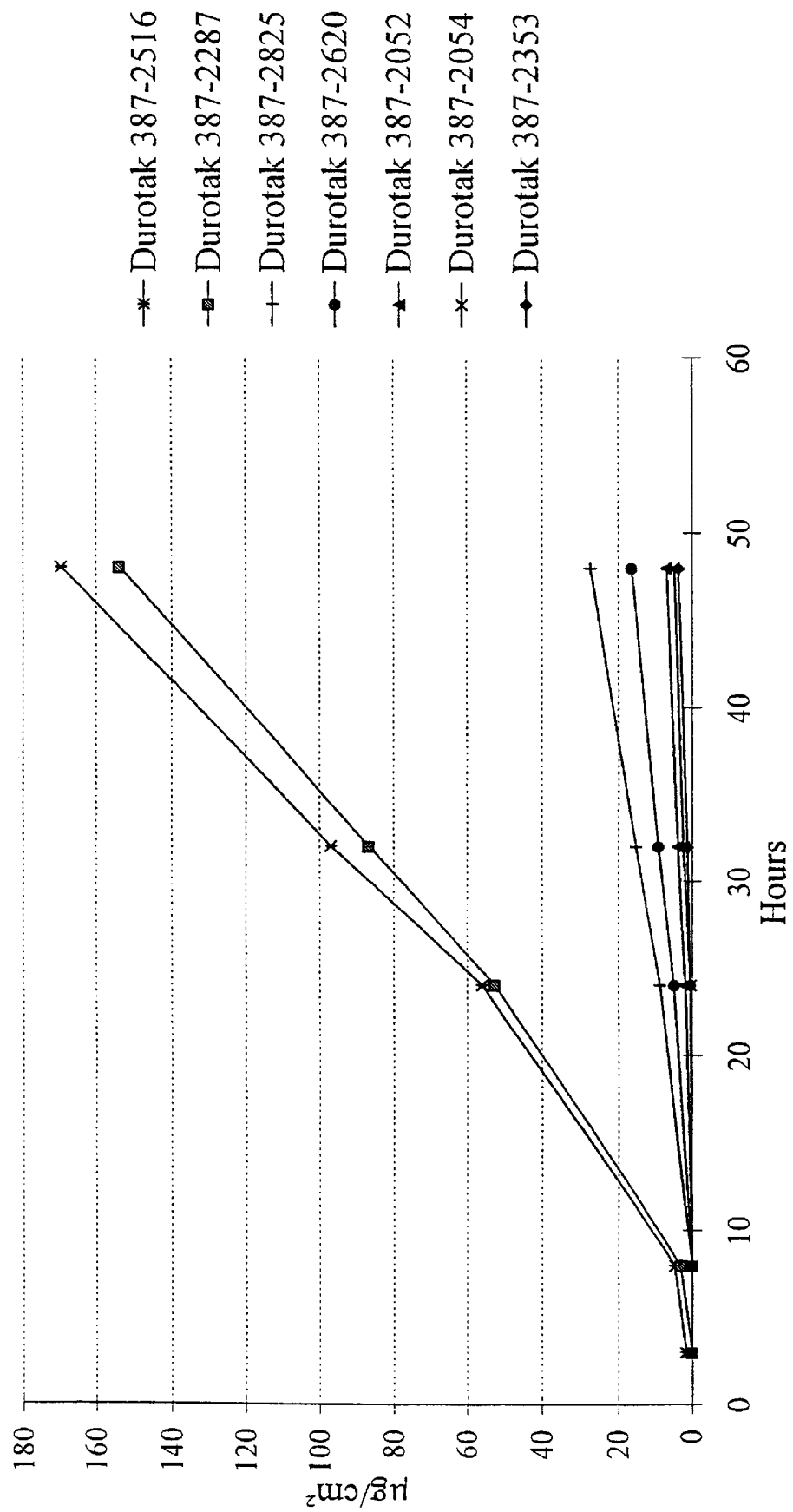

In vitro dissolution studies of the transdermal drug delivery Systems 1 and 2 according to Example 3 (FIG. 4)

Patches of 7.1 cm$^2$ were applied to the disk assembly, using a suitable adhesive, with the release surface facing up. Samples were withdrawn periodically up to 24 hours. The amount of tolterodine base in the samples was determined by HPLC and the amount of tolterodine base released from the patches was expressed in mg tolterodine base per cm$^2$. The result shows that it is possible to control the release rate of tolterodine base by changing the type of polymer.

Example 5

System 4 (drug-in-adhesive, acrylates)

Loading of acrylates with tolterodine base in different concentrations (same dry coat weight).

Patches containing different concentrations of tolterodine base in Durotak 387-2052 (1), 387-2054 (2), 387-2287 (3–7 incl.), 387-2353 (8), 87-2070 (9–12 incl.), 387-2516 (13–15 incl.), 387-2620 (18), 387-2825 (19), 87-2852 (20,21) and Röhm 2787F (24,25) were manufactured.

The figures in the brackets refer to the formulation numbers mentioned in Table 2.

Durotak 387-2052, 387-2054, 387-2287, 387-2353, 87-2070 and 387-2825:

Tolterodine base was dissolved in ethyl acetate whereafter the acrylate polymer was added.

Durotak 387-2516, 387-2620, 87-2852 and Röhm 2787F:

Tolterodine base was dissolved in the acrylate polymer.

The drug gels were each coated onto a polyester release liner (S 2016 or FL 2000-696029/3) by using the coating equipment. The laminate was dried at 80° C. (Röhm 2787F was dried at 60° C.) for 10 min. The dry coat weight was approximately 110 g/m$^2$. A backing membrane (Scotchpak 1109) was laminated onto the dried drug gel. The sheets were cut into patches and stored at 2–8° C. until use (packed in Barex pouches).

See below Table 2 for information about amount of ingredients and concentration of tolterodine base in the patches.

TABLE 2

Amount of ingredients and concentration of tolterodine

| Polymer No. | Formulation No | Tolterodine base g | Ethylacetate g | Durotak g | Conc. of tolterodine mg/cm$^2$ |
|---|---|---|---|---|---|
| D 387-2052 | 1 | 6.6 | 21.4 | 122.0 | 0.96 |
| D 387-2054 | 2 | 6.6 | 21.4 | 122.0 | 0.98 |
| D 387-2287 | 3 | 0.6 | 9.9 | 39.6 | 0.22 |
|  | 4 | 1.1 | 9.8 | 39.1 | 0.37 |
|  | 5 | 6.2 | 26.8 | 107.1 | 1.02 |
|  | 6 | 4.4 | 20.7 | 74.9 | 1.15 |
|  | 7 | 12.3 | 25.5 | 102.1 | 1.86 |
| D 387-2353 | 8 | 3.3 | 17.6 | 79.1 | 0.95 |
| D 87-2070 | 9 | 0.5 | 7.9 | 41.6 | 0.21 |
|  | 10 | 1.0 | 7.8 | 41.2 | 0.36 |
|  | 11 | 5.7 | 21.3 | 112.9 | 0.94 |
|  | 12 | 6.6 | 11.6 | 61.8 | 1.85 |
| D 387-2516 | 13 | 4.6 | — | 95.4 | 0.97 |
|  | 14 | 6.9 | — | 93.1 | 1.36 |
|  | 15 | 9.2 | — | 90.8 | 1.84 |
|  | 16 | 38.6 | — | 361.4 | 2.08 |
|  | 17 | 4.8 | — | 95.2 | 1.08 |
| D 387-2620 | 18 | 4.1 | — | 95.8 | 1.03 |
| D 387-2825 | 19 | 4.4 | 14.3 | 81.3 | 1.03 |
| D 87-2852 | 20 | 5.4 | — | 134.6 | 1.03 |
|  | 21 | 6.2 | — | 73.8 | 1.74 |
| MA-24 | 22 | 6.8 | 46.6 | 186.6 | 0.95 |
|  | 23 | 6.8 | 22.6 | 90.6 | 1.55 |
| Rohm 2787F | 24 | 9.1 | — | 130.9 | 1.19 |
|  | 25 | 10.4 | — | 69.6 | 2.15 |

D = Durotak

Example 6

System 5 (drug-in-adhesive, polyisobutylene)

Loading of polyisobutylene with tolterodine base in two different concentrations (same dry coat weight).

Patches containing tolterodine base in MA-24 (22,23) were manufactured.

The figures in the brackets refer to the formulation numbers mentioned in Table 2 above.

Tolterodine base was dissolved in ethyl acetate whereafter the MA-24 polymer was added.

The drug gel was coated onto a polyester release liner (S 2016) by using the coating equipment. The laminate was dried at 80° C. for 10 min. The dry coat weight was approximately 110 g/m$^2$. A backing membrane (Scotchpak 1109) was laminated onto the dried drug gel. The sheets were cut into patches and stored at 2–8° C. until use (packed in Barex pouches).

See Table 2 above for information about amount of ingredients and concentration of tolterodine base in the patches.

Example 7

In vitro dissolution studies of the transdermal drug delivery Systems 4 and 5 according to Examples 5 and 6 (FIGS. 5–9). Formulations Nos 1–13 incl. and 18–19 were used (Table 2).

Patches of 10 cm² were applied to the disk assembly, using a suitable adhesive, with the release surface facing up. Samples were withdrawn periodically up to 24 hours. The amount of tolterodine base in the samples was determined by HPLC and the amount of tolterodine base released from the patches was expressed in mg tolterodine base per cm². It can be seen from the results that different release profiles can be obtained by using different polymers. It can also be seen that within each polymer it is possible to obtain different release profiles by varying the concentration.

Example 8

In vitro skin permeation studies of the transdermal drug delivery Systems 4 and 5 according to Examples 5 and 6 (FIGS. 10–14). Formulations Nos 1–13 incl. and 18–19 were used (Table 2).

In vitro skin permeation of tolterodine base through dermatomed pigskin was investigated using Franz diffusion cells. Samples were withdrawn periodically up to 48 hours. The amount of tolterodine base in the samples was determined by HPLC.

The cumulative amount of tolterodine base in the receptor solution versus time is shown in FIGS. 10–14. The fluxes are in the range from 0.1–5.5 µg/cm²/h. It can be seen from the results that different fluxes can be obtained by using different polymers. Also it can be seen that higher fluxes are obtained with higher tolterodine base concentrations in the conducted experiments.

Example 9

System 6 (drug-in-adhesive, acrylate)

Loading of acrylate with different dry coat weights with the same concentration of tolterodine base in all patches.

Patches with tolterodine base in Durotak 87-2070 (coat weights were approximately 50, 75 and 110 g/m² respectively) were manufactured according to System 4, Example 5.

See below Table 3 for information about amount of ingredients, coat weights and concentration of tolterodine base in the patches.

TABLE 3

Ingredients, coat weights and concentration of tolterodine.

| Durotak No. | Laminate No. | Coat weight g/m² | Tolterodine base g | Ethylacetate g | Durotak g | Conc. mg/cm² |
|---|---|---|---|---|---|---|
| 87-2070 | 26 | 50 | 2.4 | 6.0 | 31.6 | 0.68 |
| | 27 | 75 | 1.6 | 6.1 | 32.3 | 0.66 |
| | 28 | 110 | 1.1 | 6.2 | 32.7 | 0.64 |

Example 10

Figure 15:
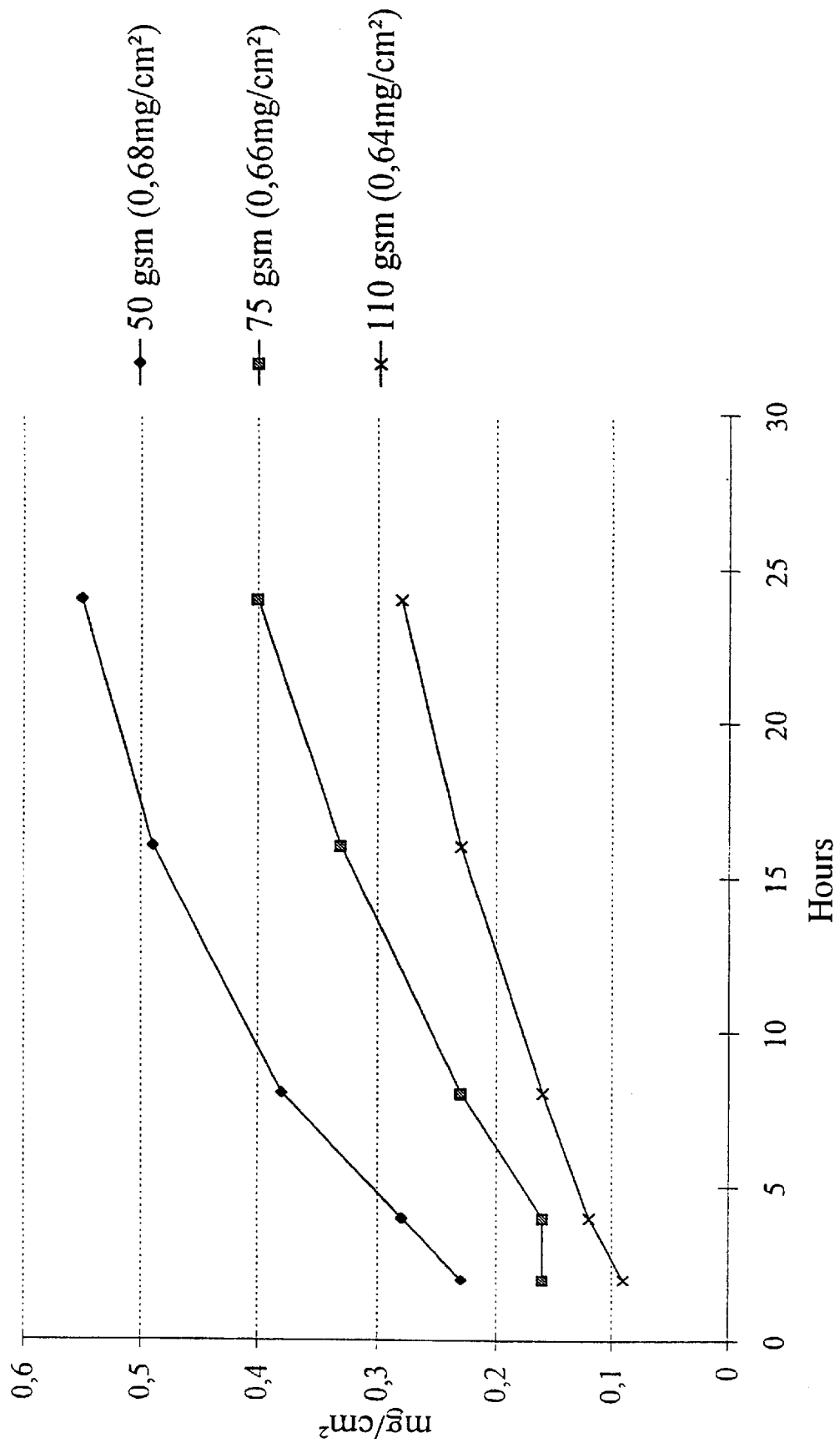
FIG. 15 is a diagram showing in vitro dissolution of tolterodine base from different transdermal systems according to Example 10.

In vitro dissolution studies of the transdermal drug delivery System 6 according to Example 9 (FIG. 15)

Patches of 10 cm² were applied to the disk assembly, using a suitable adhesive, with the release surface facing up. Samples were withdrawn periodically up to 24 hours. The amount of tolterodine base in the samples was determined by BPLC and the amount of tolterodine base released from the patches was expressed in mg tolterodine base per cm². The results show that different release profiles can be obtained by varying the coat weight. It can be seen that the highest release of tolterodine base is obtained with the lowest coat weight.

Example 11

Figure 16:
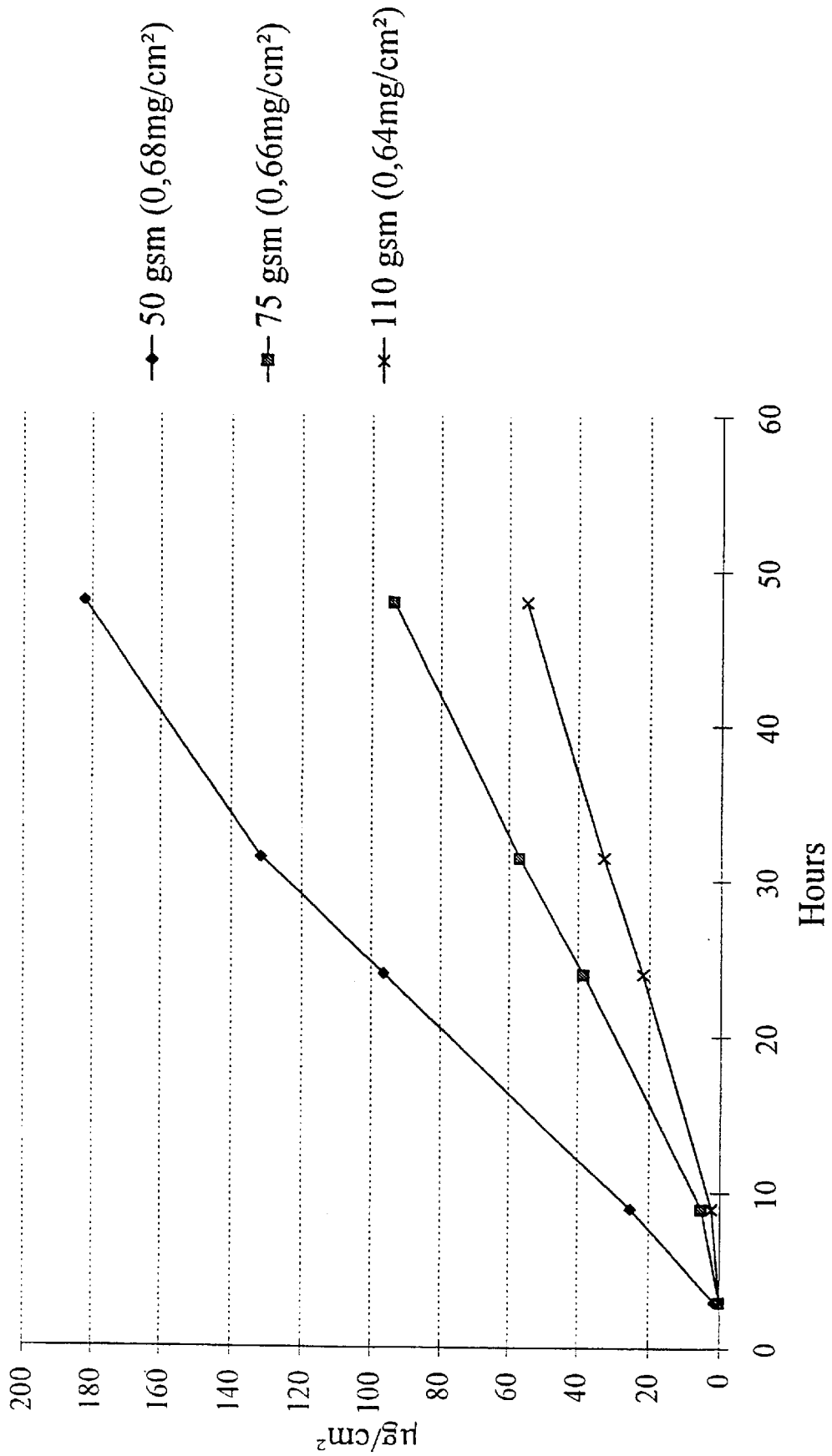
FIG. 16 is a diagram showing in vitro skin permeation of tolterodine base from different transdermal systems according to Example 11.

In vitro skin permeation studies of the transdermal drug delivery System 6 according to Example 9 (FIG. 16).

In vitro skin permeation of tolterodine base through dermatomed pigskin was investigated using Franz diffusion cells. Samples were withdrawn periodically up to 48 hours. The amount of tolterodine base in the samples was determined by HPLC.

The cumulative amount of tolterodine base in the receptor solution versus time is shown in FIG. 16. The fluxes are in the range from 1,3–4,7 µg/cm²/h. It can be seen from the results that different fluxes can be obtained by using different coat weights. Also it can be seen that the highest flux is obtained with the lowest coat weight.

Example 12

System 7 (drug-in-adhesive, acrylates)

Comparison of Durotak 387-2287 with and without crosslinker (XL) added.

Patches with tolterodine base in Durotak 387-2287 were manufactured according to System 4. Durotak 2287 does not contain XL per se but was in this experiment added two different concentrations of XL.

Addition of 0.5% polybutyltitanate (PBT) to Durotak 387-2287:

0,33 g PBT was dissolved in 5,2 g heptane. 36,0 g ethanol was added to 130,8 g Durotak 387-2287. The mixture of ethanol and Durotak 387-2287 was heated to about 60° C. whereafter the XL mixture was added.

Addition of 1.0% PBT to Durotak 387-2287:

0.64 g PBT was dissolved in 10.0 g heptane. 34.4 ethanol was added to 124,8 g Durotak 387-2287. The mixture of ethanol and Durotak 387-2287 was heated to about 60° C. whereafter the XL mixture was added.

The concentration of tolterodine base in the patches was about 2 mg/cm² and the coat weight was about 100 g/m².

See below Table 4 for information about amount of ingredients, type of crosslinkers, and concentration of tolterodine base in the patches.

TABLE 4

Ingredients, type of crosslinkers and concentration of tolterodine.

| Durotak No. | Laminate No. | Crosslinker % (dry) | Tolterodine base g | Ethylacetate g | Durotak g | Conc. mg/cm² |
|---|---|---|---|---|---|---|
| 387-2287 | 29 | — | 7.0 | 15.8 | 57.2 | 1.79 |
| 387-2287 | 30 | 0.5% PBT* | 12.6 | — | 137.4 (incl. XL) | 1.71 |
| 387-2287 | 31 | 1% PBT* | 12.2 | — | 137.8 (incl. XL) | 1.76 |

*PBT = Polybutyltitanate

Example 13

Figure 17:
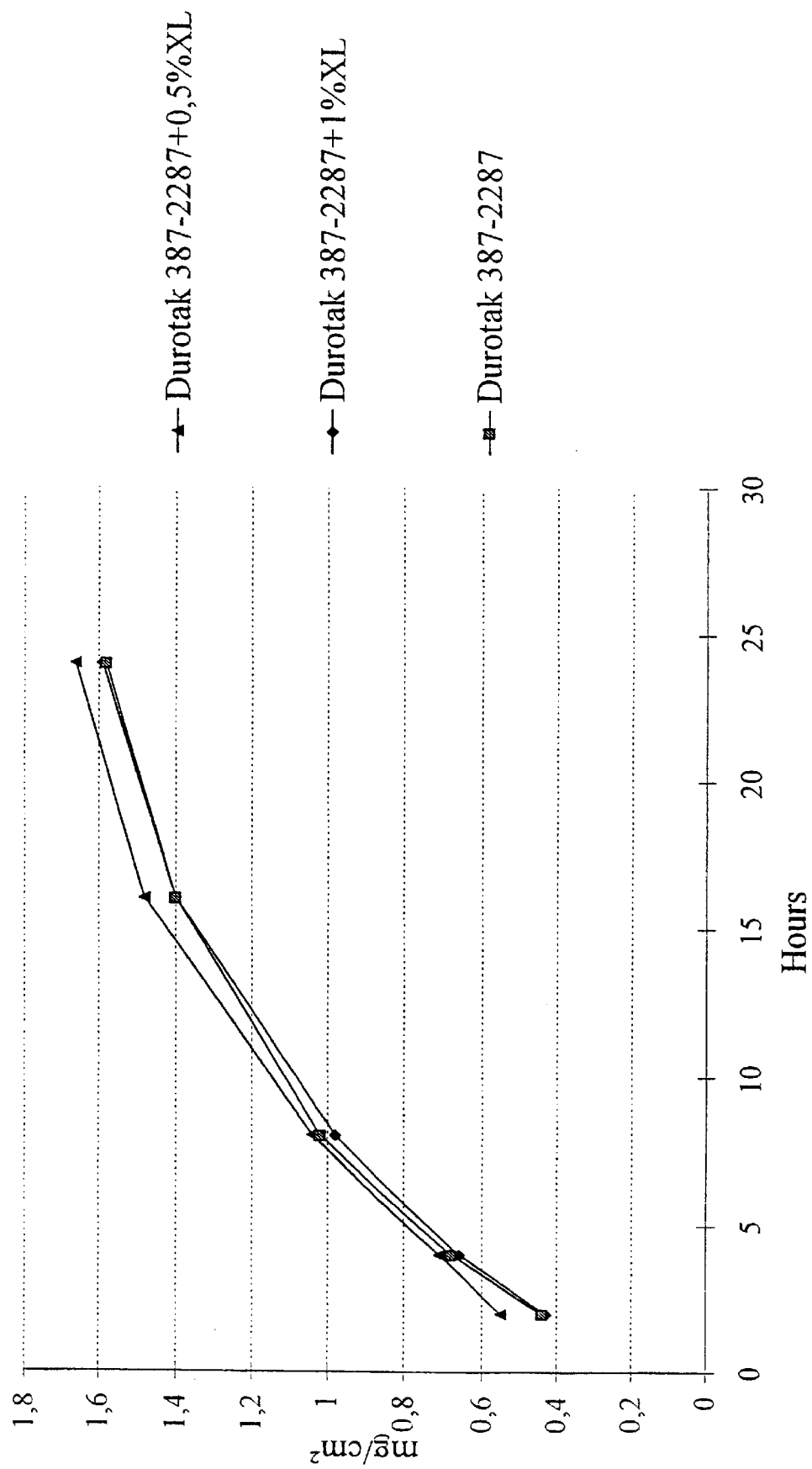
FIG. 17 is a diagram showing in vitro dissolution of tolterodine base from different transdermal systems according to Example 13.

In vitro dissolution studies of the transdermal drug delivery System 7 according to Example 12 (FIG. 17).

Patches of 10 cm² were applied to the disk assembly, using a suitable adhesive, with the release surface facing up. Samples were withdrawn periodically up to 24 hours. The amount of tolterodine base in the samples was determined by HPLC and the amount of tolterodine base released from the patches was expressed in mg tolterodine base per cm². The results show that the same dissolution profiles are obtained regardless of the added crosslinker. It may be important to add crosslinking agents to the formulations in order to obtain optimal adhesiveness and cohesion.

Example 14

System 8 (drug-in-adhesive, acrylate)

Loading of acrylate with tolterodine L-tartrate

The gels were prepared by suspending the tolterodine L-tartrate into the polymer Durotak 387-2287. A 9.4M NaOH solution (in water) corresponding to 2 equimolar was added to some of the gel in order to try to convert the tartrate into base. Also 9.4M NaOH solution (in water) was added to tolterodine base/Durotak 387-2287 gel in order to evaluate if the dissolution profile was changed with the addition of NaOH.

The patches were coated according to System 4, Example 5.

See below Table 5 for information about amount of ingredients, and concentration of tolterodine L-tartrate in the patches.

TABLE 5

Ingredients and concentration of tolterodine L-tartrate.

| Polymer No. | Laminate No. | NaOH ml | Tolterodine g | Ethylacetate g | Durotak g | Conc. mg/cm² |
|---|---|---|---|---|---|---|
| D 387-2287 | 32 | — | 5.2 (tartrate) | 15.3 | 59.5 | 0.75 |
|  | 33 | 1.2 | 2.6 (tartrate) | 10.3 | 29.8 | 0.99 |
|  | 34 | 0.6 | 1.8 (base) | 7.6 | 30.6 | 0.97 |
| MA-24 | 35 | — | 3.3 (tartrate) | 15.5 | 61.2 | 0.79 |
|  | 36 | 1.5 | 3.3 (tartrate) | 15.5 | 61.2 | 0.87 |

Example 15

System 9 (drug-in-adhesive, polyisobutylene)

Loading of polyisobutylene with tolterodine L-tartrate

The gels were prepared by suspending the tolterodine L-tartrate into the polymer MA-24. A 9.4M NaOH solution (in water) corresponding to 2 equimolar was added to some of the gel in order to convert the tartrate into base.

The patches were coated according to System 5, Example 6.

See above Table 5 for information about amount of ingredients and concentration of tolterodine L-tartrate in the patches.

Example 16

Figure 18:
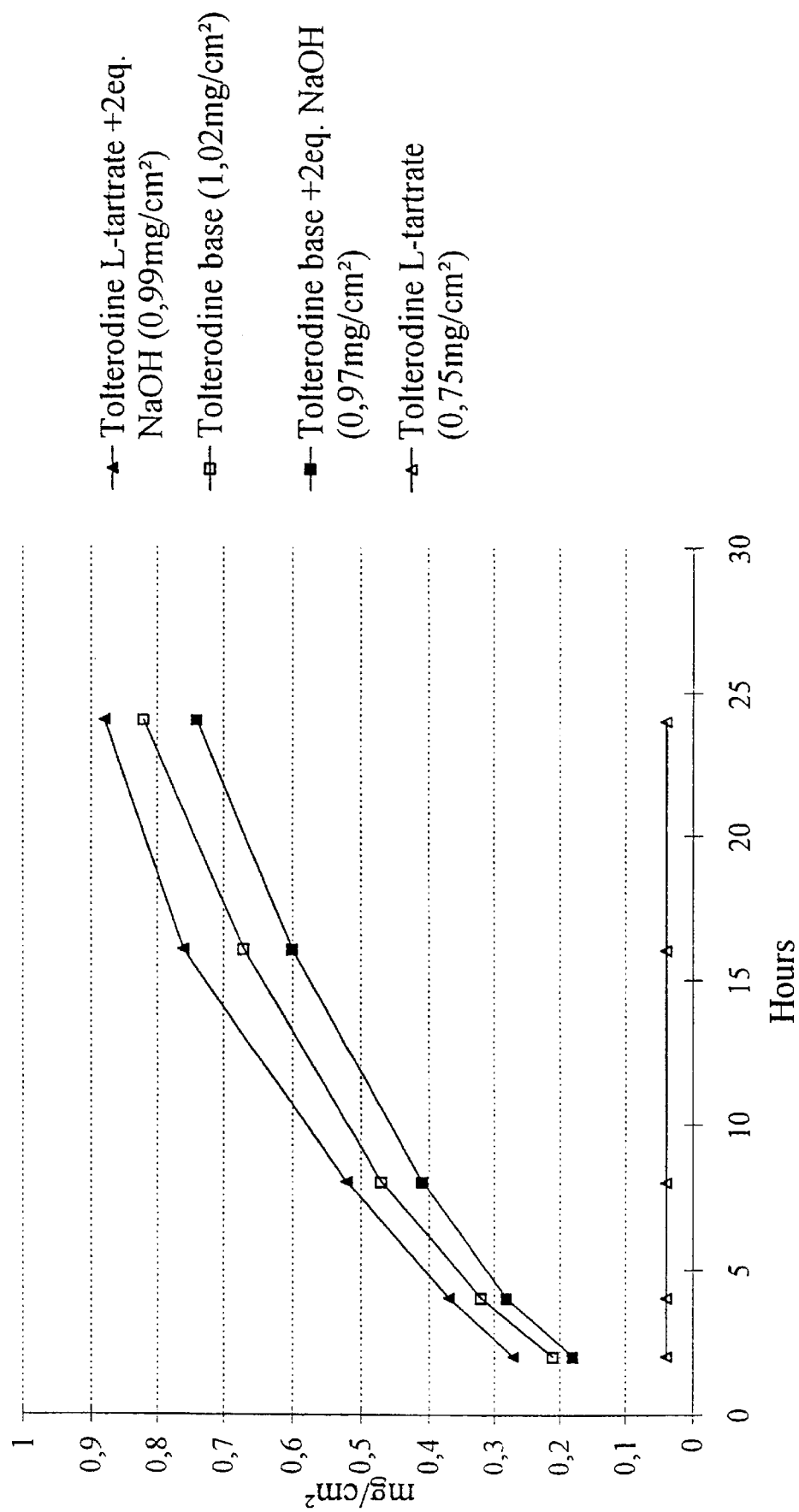
FIGS. 18 and 19 are diagrams showing in vitro dissolution of tolterodine L-tartrate and tolterodine base from different transdermal systems according to Example 16.
Figure 19:
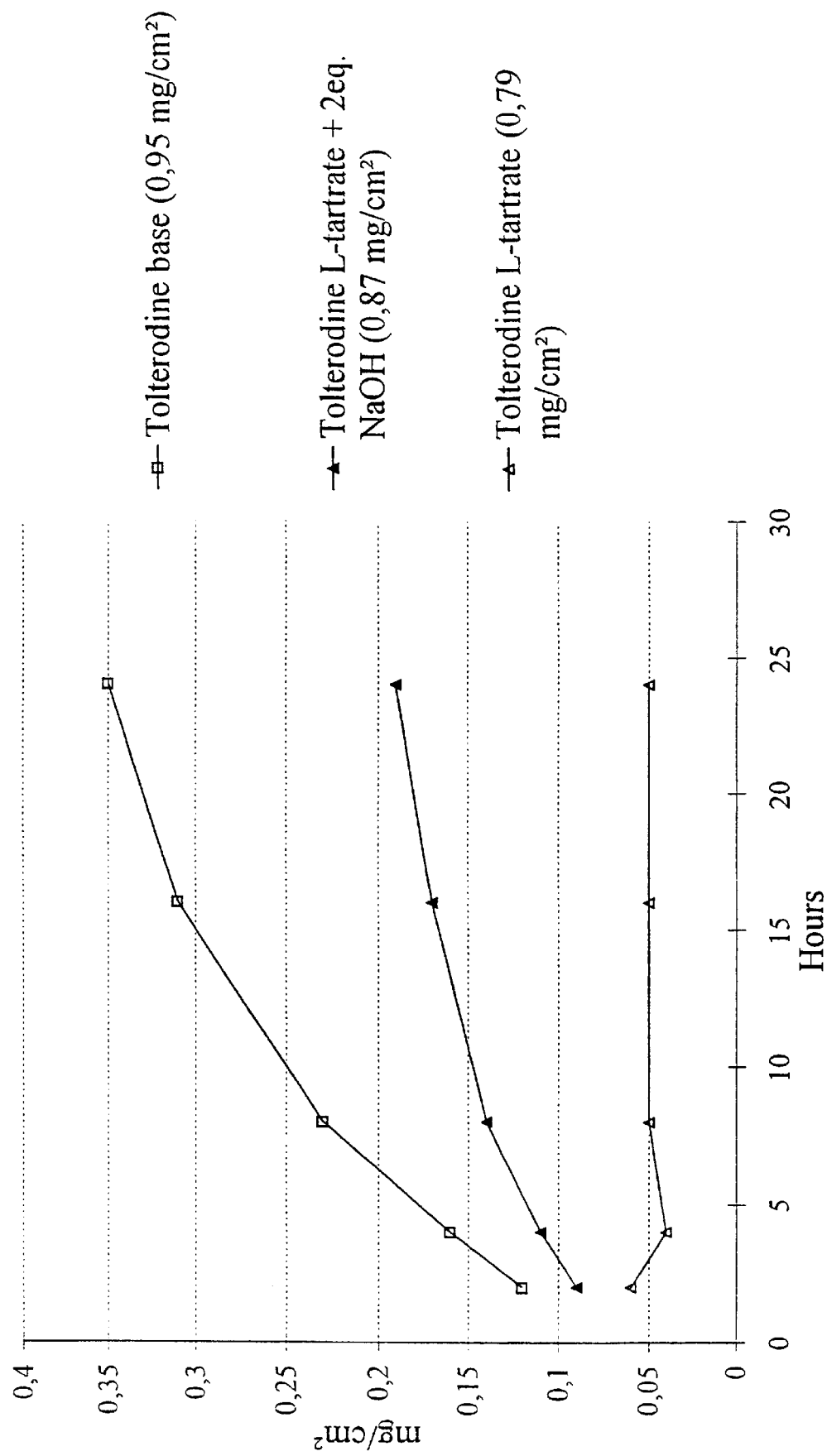

In vitro dissolution studies of the transdermal drug delivery Systems 8 and 9 according to Examples 14 and 15 (FIG. 18 and 19). Laminate No 5 according to Example 5 containing tolterodine base in Durotak 387-2287 was used for comparison.

Patches of 10 cm² were applied to the disk assembly, using a suitable adhesive, with the release surface facing up. Samples were withdrawn periodically up to 24 hours. The amount of tolterodine (calculated as base) in the samples was determined by HPLC and the amount of tolterodine base released from the patches was expressed in mg tolterodine base per cm². The results show that it is possible to convert most of the tolterodine L-tartrate to tolterodine base when adding NaOH to the gel containing tolterodine L-tartrate and polymer.

Example 17

Figure 20:
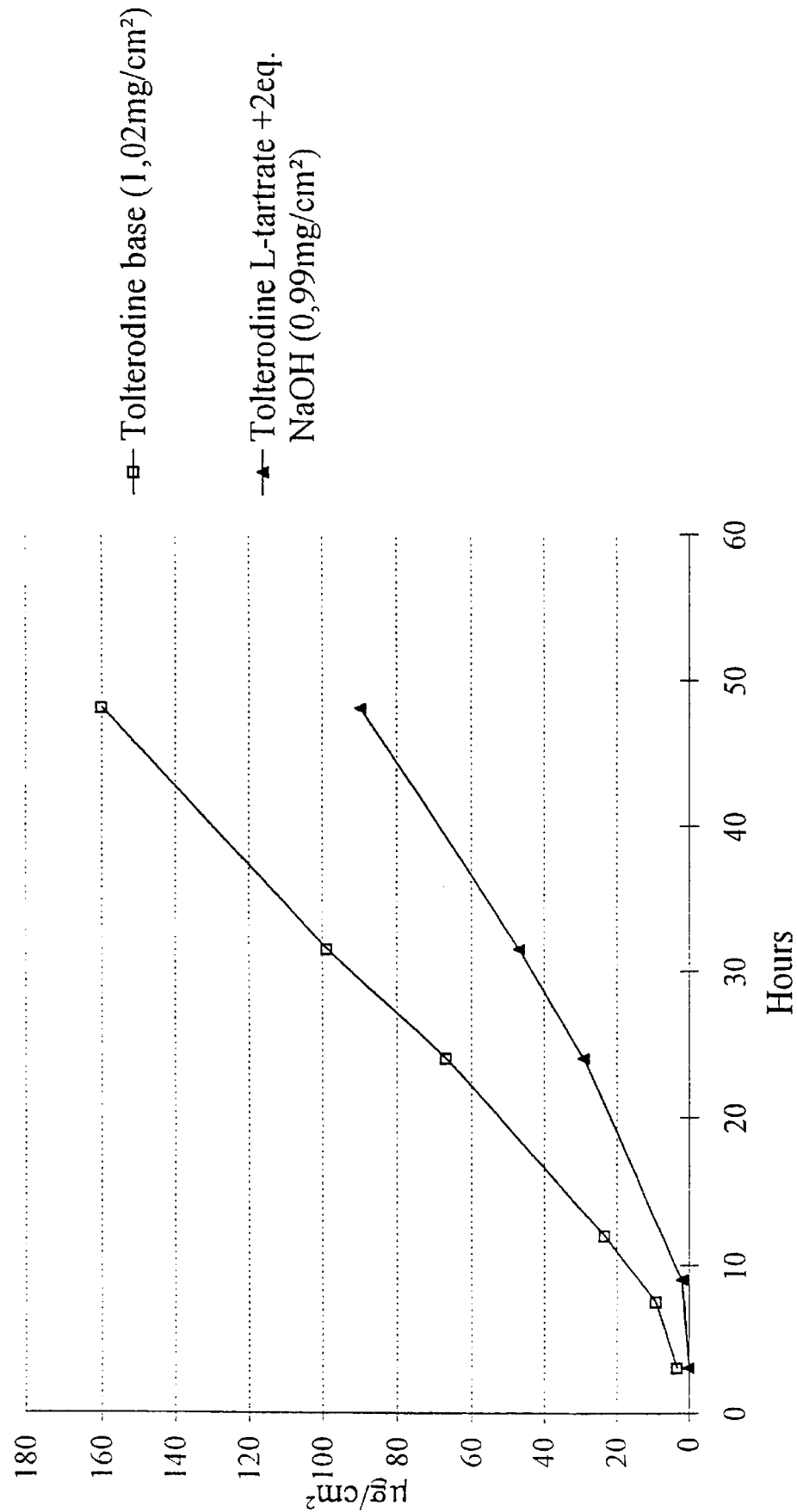
FIGS. 20 and 21 are diagrams showing in vitro skin permeation of tolterodine L-tartrate and tolterodine base from different transdermal systems according to Example 17.
Figure 21:
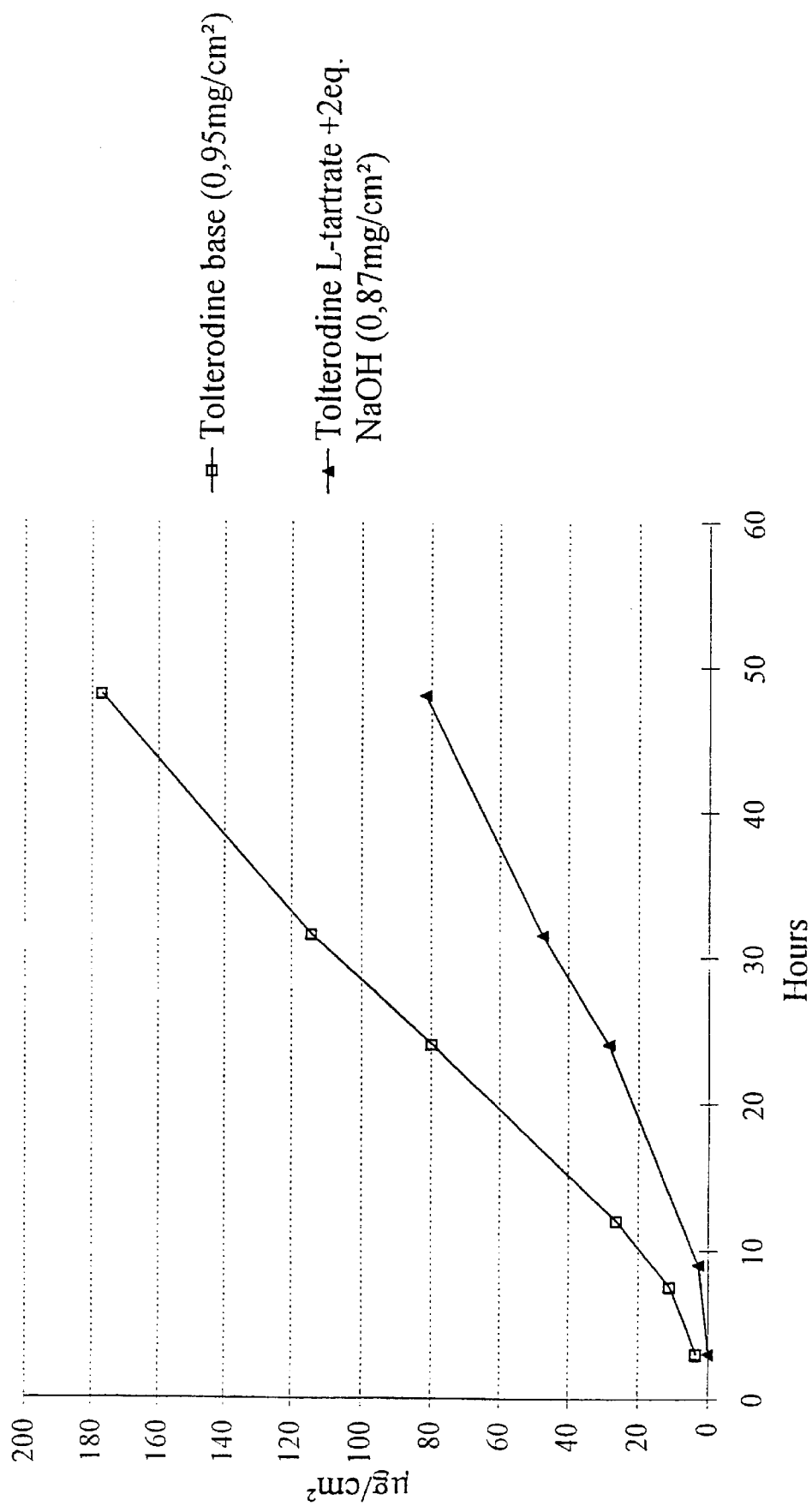

In vitro skin permeation studies of the transdermal drug delivery Systems 8 and 9 according to Example 14 and 15 (FIG. 20 and 21).

In vitro skin permeation of tolterodine base through dermatomed pigskin was investigated using Franz diffusion cells. Samples were withdrawn periodically up to 48 hours. The amount of tolterodine (calculated as base) in the samples was determined by BPLC.

The cumulative amount of tolterodine base in the receptor solution versus time is shown in FIG. 20 and 21. The results show that it is possible to convert most of the tolterodine L-tartrate to tolterodine base when adding NaOH to the gel containing tolterodine L-tartrate and polymer.

Example 18

Stability studies were carried out on formulations Nos 1, 2, 6, 8, 13, IS and 19 according to Example 5. The patches were stored at 25° C./60% RH and 40° C./75% RH and quantitative determination of tolterodine base was done by HPLC after 0, 1, 2 and 3 months. The results are shown in below Table 6. It can be seen that the formulations are stable after 3 months' storage. However, a slight decrease in tolterodine base content is might be seen after 3 months for Durotak 387-2353.

TABLE 6

Stability of tolterodine base in different Durotak polymers.
Concentration 1 mg/cm²
Coat weight 100 g/cm²

| Months | Durotak 387–2052 mg/cm² | Durotak 387–2054 mg/cm² | Durotak 387–2516 mg/cm² | Durotak 387–2620 mg/cm² | Durotak 387–2825 mg/cm² | Durotak 387–2353 mg/cm² | Durotak 387–2287 mg/cm² |
|---|---|---|---|---|---|---|---|
| Initial 1 month | 0,96 | 0,98 | 0,97 | 1,03 | 1,03 | 0,95 | 1,15 |
| 25° C. 60% RH | 0,99 | 1,05 | 1,06 | 1,00 | 1,04 | 0,93 | 1,05 |
| 40° C. 75% RH | 0,96 | 1,02 | 1,05 | 0,98 | 1,08 | 0,83 | 1,13 |

TABLE 6-continued

Stability of tolterodine base in different Durotak polymers.
Concentration 1 mg/cm²
Coat weight 100 g/cm²

| Months | Durotak 387–2052 mg/cm² | Durotak 387–2054 mg/cm² | Durotak 387–2516 mg/cm² | Durotak 387–2620 mg/cm² | Durotak 387–2825 mg/cm² | Durotak 387–2353 mg/cm² | Durotak 387–2287 mg/cm² |
|---|---|---|---|---|---|---|---|
| 2 months | | | | | | | |
| 25° C. 60% RH | 0,95 | 0,97 | 1 | 0,88 | 0,97 | 0,92 | 1,07 |
| 40° C. 75% RH | 0,91 | 0,92 | 0,96 | 0,88 | 0,91 | 0,88 | 1,03 |
| 3 months | | | | | | | |
| 25° C. 60% RH | 0,98 | 1 | 1,02 | 0,83 | 0,99 | 0,9 | 1,14 |
| 40° C. 75% RH | 1,04 | 0,96 | 0,92 | 0,87 | 0,99 | 0,73 | 1,13 |

Example 19

System 10 (drug-in-adhesive, acrylates). Up-scaling of formulation.

Loading of acrylate with tolterodine base

Patches containing tolterodine base in Durotak 387-2516 (formulations Nos 16 and 17 according to Table 2) were manufactured.

Tolterodine base was dissolved directly in the Durotak 387-2516 polymer.

The drug gel was coated onto a polyester release liner (FL 2000-696029/3) by using the Laboratory Coater. The laminate was dried at 40/80/80° C. for 10 min. The dry coat weight was approximately 110 g/m². A backing membrane (Scotchpak 1109) was laminated onto the dried drug gel. The laminate was cut into patches and stored at 2–8° C. until use (packed in Barex pouches).

See Table 2 above for information about amount of ingredients and concentration of tolterodine base in the patches.

Example 20

Figure 22:
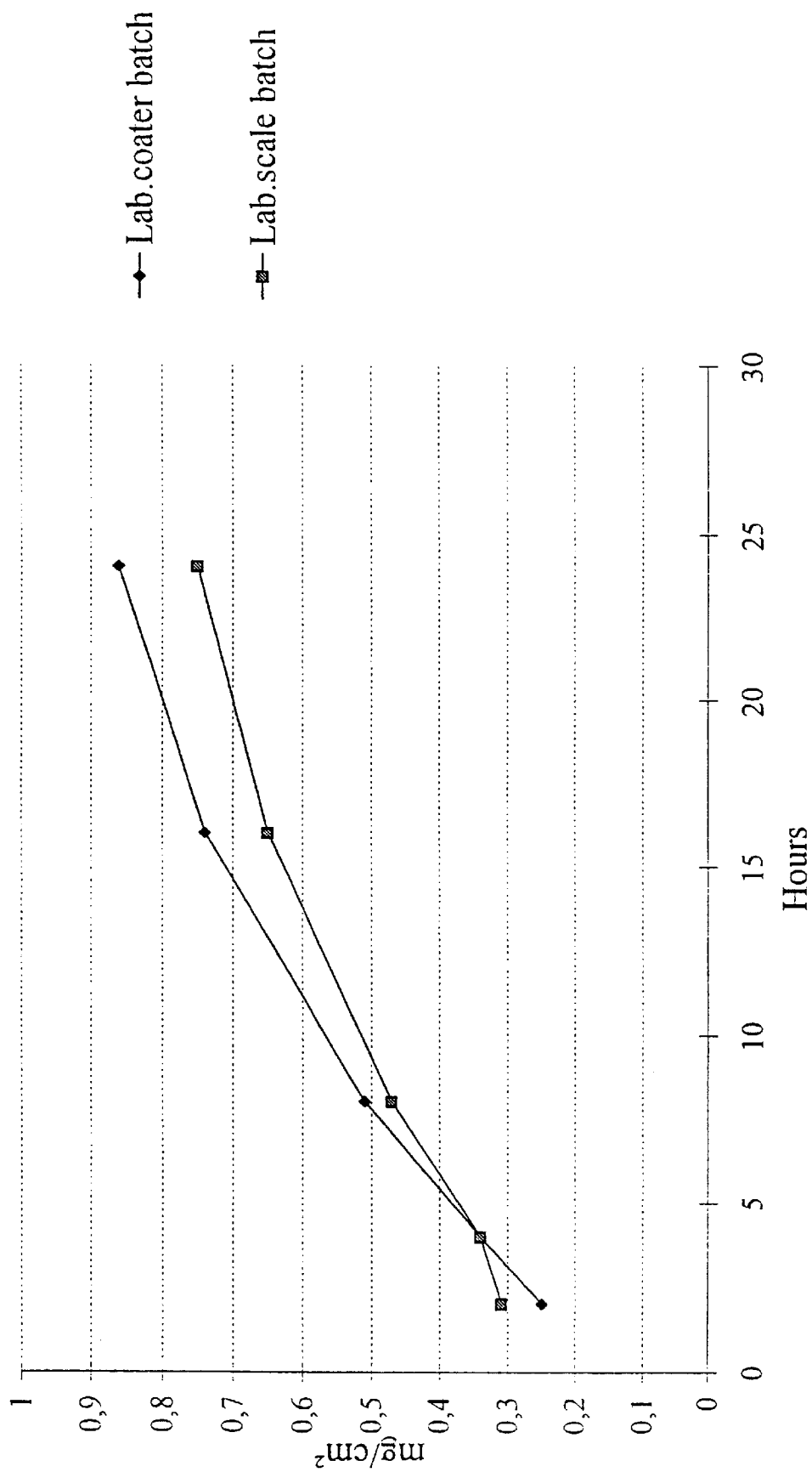
FIG. 22 is a diagram showing in vitro dissolution of tolterodine base from different transdermal systems according to Example 20.

In vitro dissolution studies of transdermal drug delivery System 10 (formulation No 17 according to Example 19 (FIG. 22). Laminate No 13 according to Example 5 containing tolterodine base in Durotak 387-2516 (laboratory scale) was used for comparison.

Patches of 10 cm² were applied to the disk assembly using a suitable adhesive with the release surface facing up. Samples were withdrawn periodically up to 24 hours. The amount of tolterodine base in the samples was determined by PLC and the amount of tolterodine base released from the patches was expressed in mg tolterodine base per cm². The results show that the same dissolution profiles are obtained (without regard to whether the patches are manufactured in laboratory scale or in the Laboratory Coater).

Example 21

Figure 23:
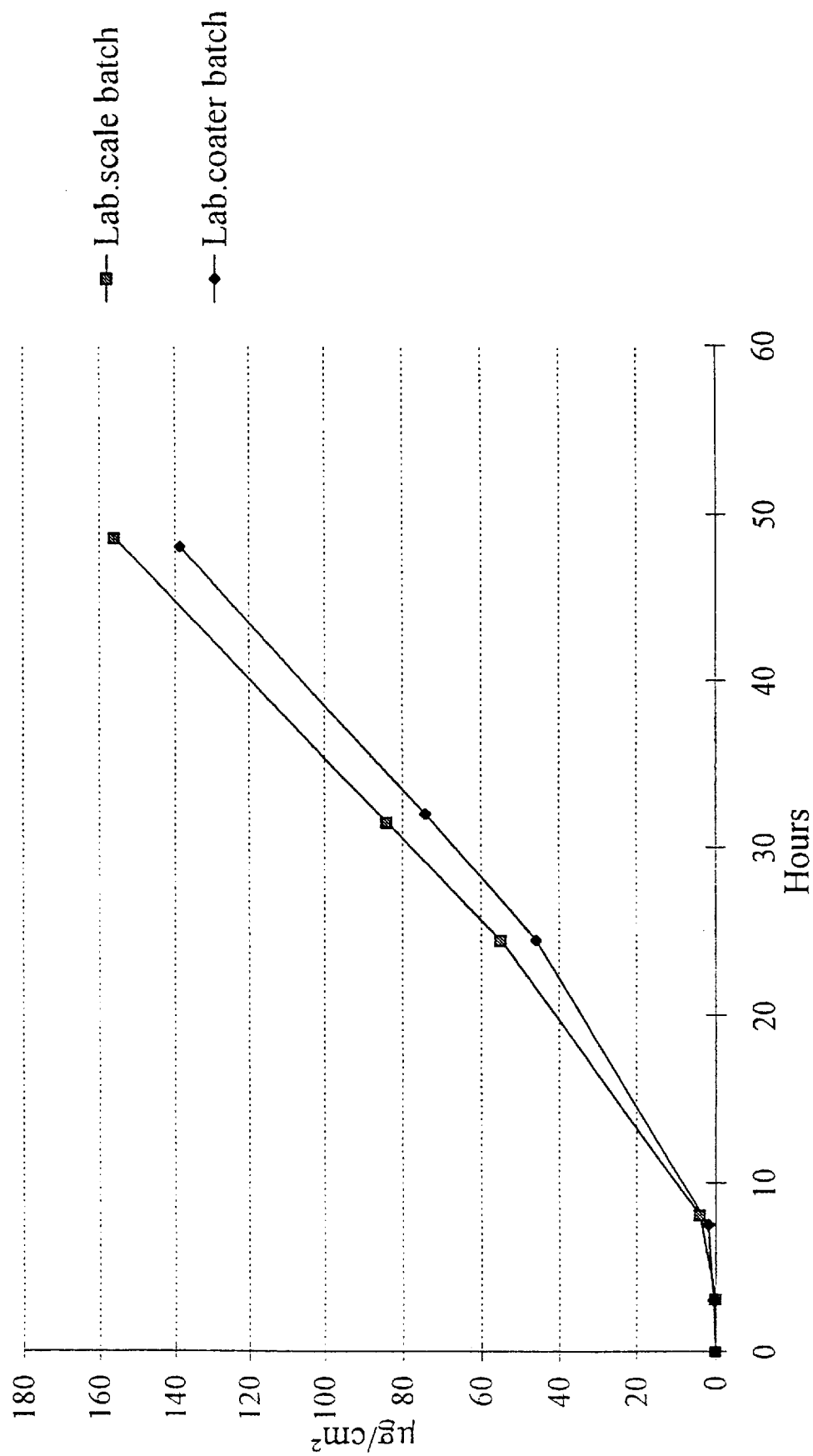
FIG. 23 is a diagram showing in vitro skin permeation of tolterodine base from different transdermal systems according to Example 21.

In vitro skin permeation studies of the transdermal drug delivery System 10 (laminate No 17) according to Example 19 (FIG. 23). Formulation No 13 containing tolterodine base in Durotak 387-2516 (laboratory scale) was used for comparison.

In vitro skin permeation of tolterodine base through dermatomed pigskin was investigated using Franz diffusion cells. Samples were withdrawn up to 48 hours. The amount of tolterodine base in the samples was determined by BPLC.

The cumulative amount of tolterodine base in the receptor solution versus time is shown in FIG. 23. The results show that the same profiles are obtained (regardless of whether the patches are made in laboratory scale or in the Laboratory Coater).

Example 22

In vivo skin permeation study of transdermal drug delivery System 10 according to Example 19. (Formulation No. 16, Table 2.)

In vivo skin permeation of tolterodine base was investigated (1 person). The is 10 cm² patch was applied on the upper arm for 24 hours whereafter the residual amount of tolterodine base in the patch was analysed. The result showed that about 4.8 mg tolterodine base, corresponding to about 7.2 mg tolterodine L-tartrate was released from the patch and thus permeated into the skin.

Example 23

Primary skin irritation study in the rabbit and test for delayed contact hypersensitivity using the Guinea Pig Maximization Test (performed by Scantox, Denmark).

The primary skin irritating effect of tolterodine base and tolterodine L-tartrate was investigated according to the method in the OECD Guideline No 404, "Acute Dermal Irritation/Corrosion", 1992, and EEC Guideline B.4 "Acute Toxicity (skin irritation)", 29.12.1992 with the modification that the time of exposure in both cases were 24 hours.

0.5 g of each test material were moistened with 0.5 ml distilled water and applied on the rabbit. After 24 hours the treated skin was cleaned and after additional 1, 24, 48 and 72 hours the skin reactions were read. It was found that for tolterodine base the mean score was 0.1 for erythema and 0.0 for oedema while for tolterodine L-tartrate the mean score was 0.0 for both erythema and oedema. This means that the two compounds tolterodine base and tolterodine L-tartrate should not be classified as skin irritants.

The dermal sensitising potential of tolterodine L-tartrate was investigated according to one of the methods recommended in the OECD Guidelines No 406, "Skin Sensitization", 1992 and the ECC Guideline "EEC 92/69 part 6B", 1992. The delayed contact hypersensitivity test used was the Guinea Pig Maximization Test described by B. Magnusson and A. M. Kligman.

A 1% (w/w) test article concentration in sesame oil was used for the intradermal induction. A 25% (w/w) test article concentration in sesame oil was used for the topical induction and for the challenge application.

It was concluded that tolterodine L-tartrate did not provoke a delayed contact hypersensitivity reaction in the guinea pigs.

Example 24

Primary skin irritation study in the rabbit (performed by Scantox, Denmark).

The primary skin irritant effect of tolterodine base patches 1 m/cm$^2$, 1.5 mg/cm$^2$ and 2 mg/cm$^2$ using Durotak 387-2516 (formulations Nos 13+14+15) and placebo Durotak 387-2516 patches (same coat weight as for the active laminates) was investigated according to the method in the OECD Guideline No 404, "Acute Dermal Irritation/Corrosion", 1992, and EEC Guideline B.4 "Acute Toxicity (skin irritation)", 29.12.1992.

The tolterodine base and placebo patches were applied to the rabbits. After 4 hours of exposure the test articles were removed and the skin was examined 1, 24, 48 and 72 hours and up to 7 days after termination of exposure. It was found that for tolterodine base patches 1 mg/cm$^2$ and 1.5 mg/cm$^2$ the mean scores were 0.1 for erythema and 0.0 for oedema while for tolterodine base patches 2 mg/cm$^2$ and placebo the mean scores were 0.2 for erythema and 0.1 for oedema. This means that tolterodine base patches of 1 mg/cm$^2$, 1.5 mg/cm$^2$ and 2 mg/cm$^2$ should not be classified as skin irritants.

Example 25

System 11 (DD 01 in drug-in -adhesive, acrylate)

3.8 g of DD 01 was added to 90 g Durotak 387-2516 and 3 ml ethanol and homogenized for 5 min. The drug gel was coated onto a polyester release liner (FL 2000-696029/3) by using the coating equipment. The laminate was dried at 80° C. for 10 min. The dry coat weight was approximately 110 g/m$^2$. A backing membrane (Scotchpak 1109) was laminated onto the dried drug gel. The sheets were cut into patches and stored at 2–8° C. until use (packed in Barex pouches). The concentration of DD 01 in the patches was 0.91 mg/cm$^2$.

Figure 24:
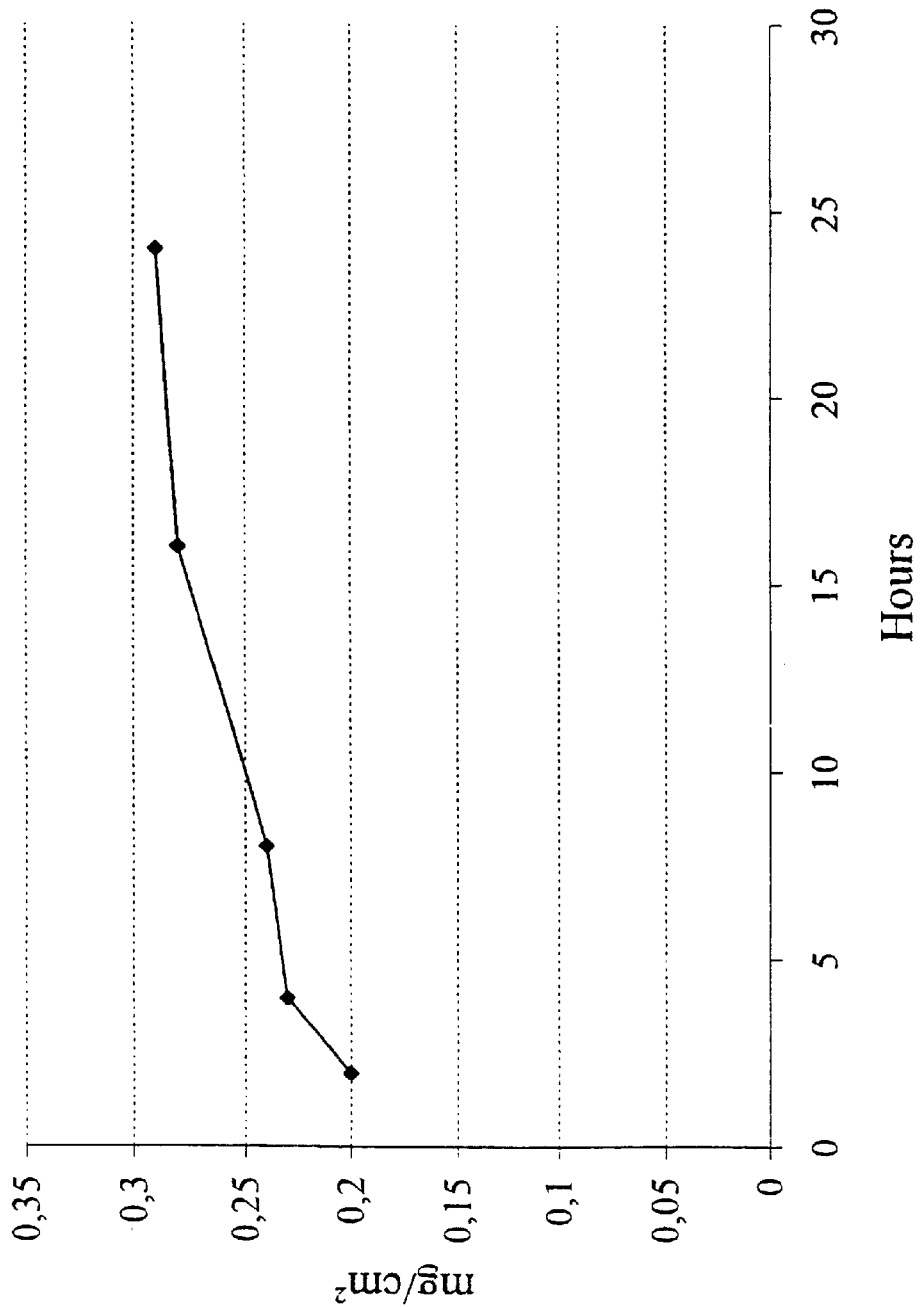
FIG. 24 is a diagram showing in vitro dissolution of DD 01 from Durotak 387-2516 according to Example 26.

In vitro dissolution study of the transdermal delivery System 11 according to Example 25 (FIG. 24).

Patches of 10 cm$^2$ were applied to the disk assembly, using a suitable adhesive, with the release surface facing up. Samples were withdrawn periodically up to 24 hours. The amount of DD 01 in the samples was determined by HPLC and the amount of DD 01 released from the patches was expressed in mg DD 01 per cm$^2$. It can be seen from the results that about 30% of DD 01 is released from the patch after 24 hours.

Example 27

Figure 25:
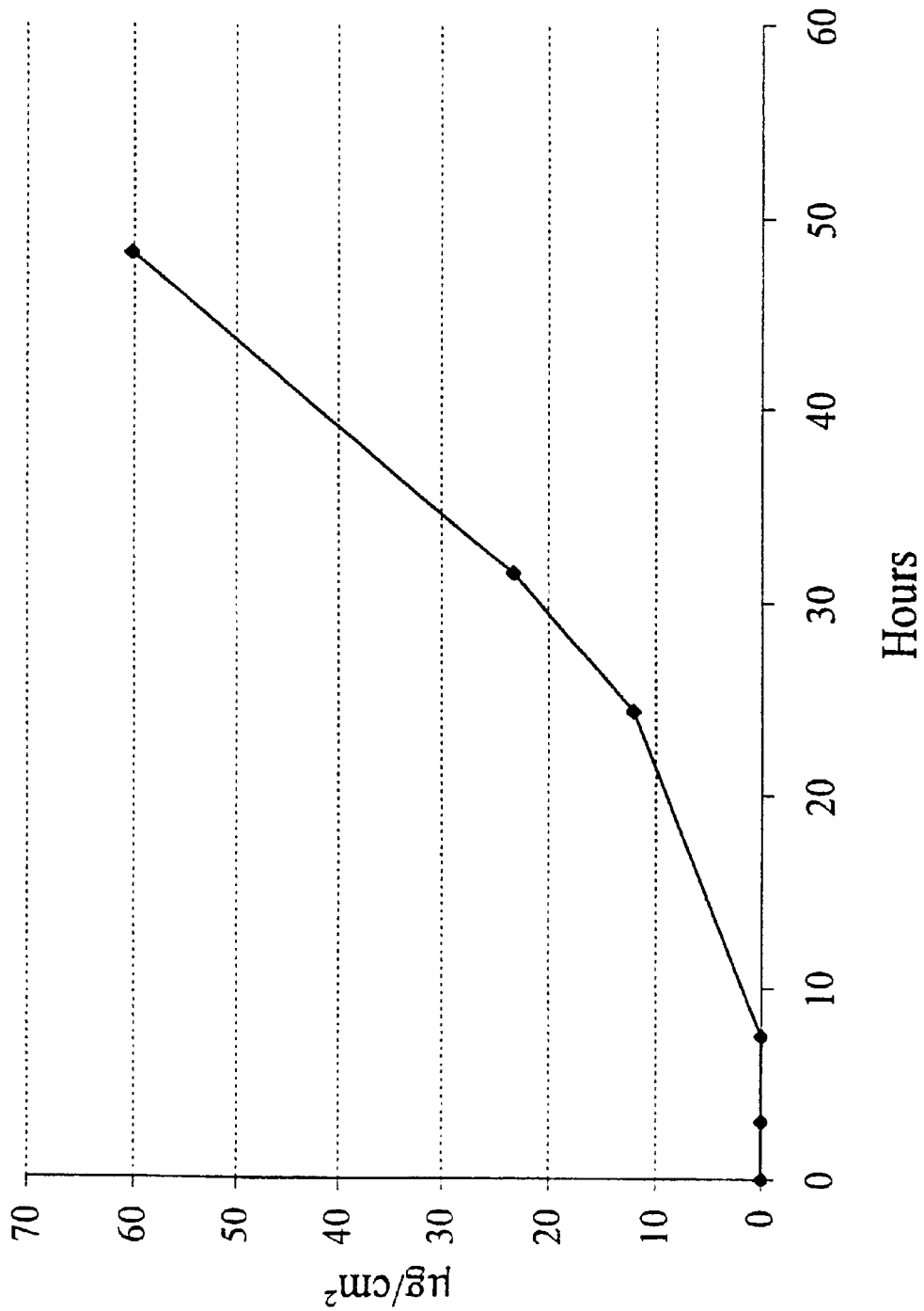
FIG. 25 is a diagram showing in vitro skin permeation of DD 01 from Durotak 387-2516 according to Example 27.

In vitro skin permeation study of the transdermal drug delivery System 11 according to Example 25 (FIG. 25).

In vitro skin permeation of DD 01 through dermatomed pigskin was investigated using Franz diffusion cells. Samples were withdrawn periodically up to 48 hours. The amount of DD 01 in the samples was determined by HPLC.

The cumulative amount of DD 01 in the receptor solution versus time is shown in FIG. 25. The obtained flux was 2 $\mu g/cm^2/h$ and the amount of DD 01 that permeated the skin was about 7%.

Example 28

System 12 (multi-laminates acrylate)

Layer b: 6 g tolterodine base was dissolved in 69 g Durotak 387-2516. The drug gel was coated onto a release liner (FL 2000-696029/3) by using the coating equipment. The laminate was dried at 80° C. for 10 min.. The dry coat weight was approximately 50 g/m$^2$. A backing membrane (Scotchpak 1109) was laminated onto the dried drug gel.

The release liner was thereafter removed and a rate controlling membrane (CoTran 9728 -19% Vinyl Acetate) was laminated onto the dried drug gel. The theoretically calculated concentration (not analysed) of tolterodine base in the laminate was 0.8 mg/cm$^2$.

Layer a: 6 g tolterodine base was dissolved in 93 g Durotak 87-2852. The drug gel was coated onto a release liner (FL 2000-696029/3) by using the coating equipment. The laminate was dried at 80° C. for 10 min. The dry coat weight was approximately 50 g/m$^2$ and the theoretically calculated concentration (not analysed) of tolterodine base in the laminate was 0.8 mg/cm$^2$. Layer a was then laminated to layer b. Layer b was then the layer nearest the backing membrane whereas layer a was the outer layer.

Example 29

System 13 (multi-laminate, acrylate)

Layer b: 6 g tolterodine base was dissolved in 93 Durotak 87-2852. The drug gel was coated onto a release liner (FL 2000-696029/3) by using the coating equipment. The laminate was dried at 80° C. for 10 min.. The dry coat weight was approximately 50 g/m$^2$. A backing membrane (Scotchpak 1109) was laminated onto the dried drug gel. The release liner was thereafter removed and a rate controlling membrane (CoTran 9728-19% Vinyl Acetate) was laminated onto the dried drug gel. The theoretically calculated concentration (not analysed) of tolterodine base in the laminate was 0.8 mg/cm$^2$.

Layer a:. 6 g tolterodine base was dissolved in 69 g Durotak 387-2516. The drug gel was coated onto a release liner (FL 2000-696029/3) by using the coating equipment. The laminate was dried at 80° C. for 10 min. The dry coat weight was approximately 50 g/m$^2$ and the theoretically calculated concentration (not analysed) of tolterodine base in the laminate was 0.8 mg/cm$^2$. Layer a was then laminated to layer b. Layer b was then the layer nearest the backing membrane whereas layer a was the outer layer.

Example 30

Figure 26:
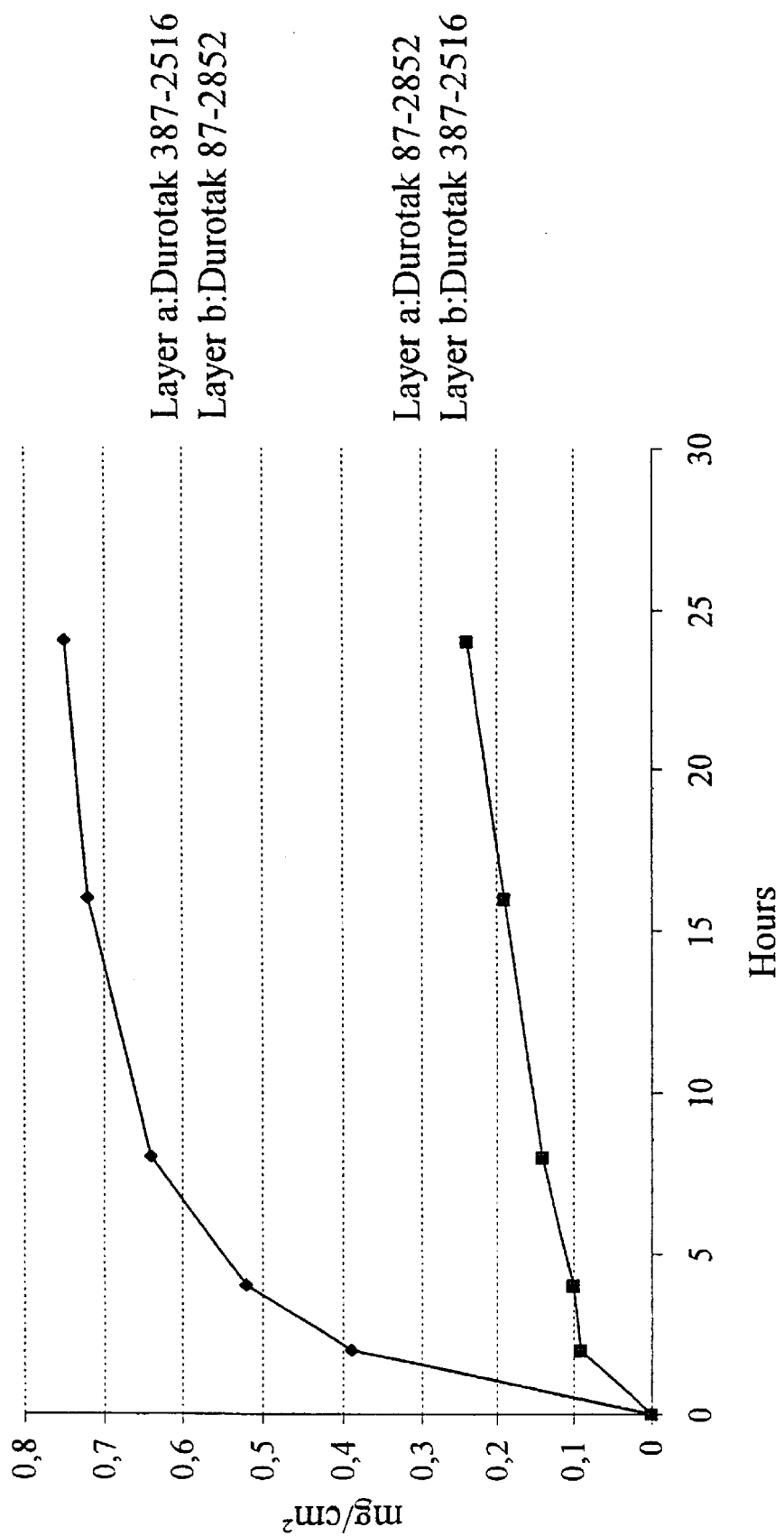
FIG. 26 is a diagram showing in vitro dissolution of tolterodine base from multilaminate patches according to Example 30.

In vitro dissolution studies of the transdermal drug delivery Systems 12 and 13 according to Example 28 and 29 (FIG. 26).

Patches of 10 cm$^2$ were applied to the convex screen, with the release surface facing up. Samples were withdrawn periodically up to 24 hours. The amount of tolterodine base in the samples was determined by HPLC and the amount of tolterodine base released from the patches was expressed in mg tolterodine base per cm$^2$. The results show that it is possible to vary the release profile by changing the polymers in the multi-laminate patch.

Example 31

Figure 27:
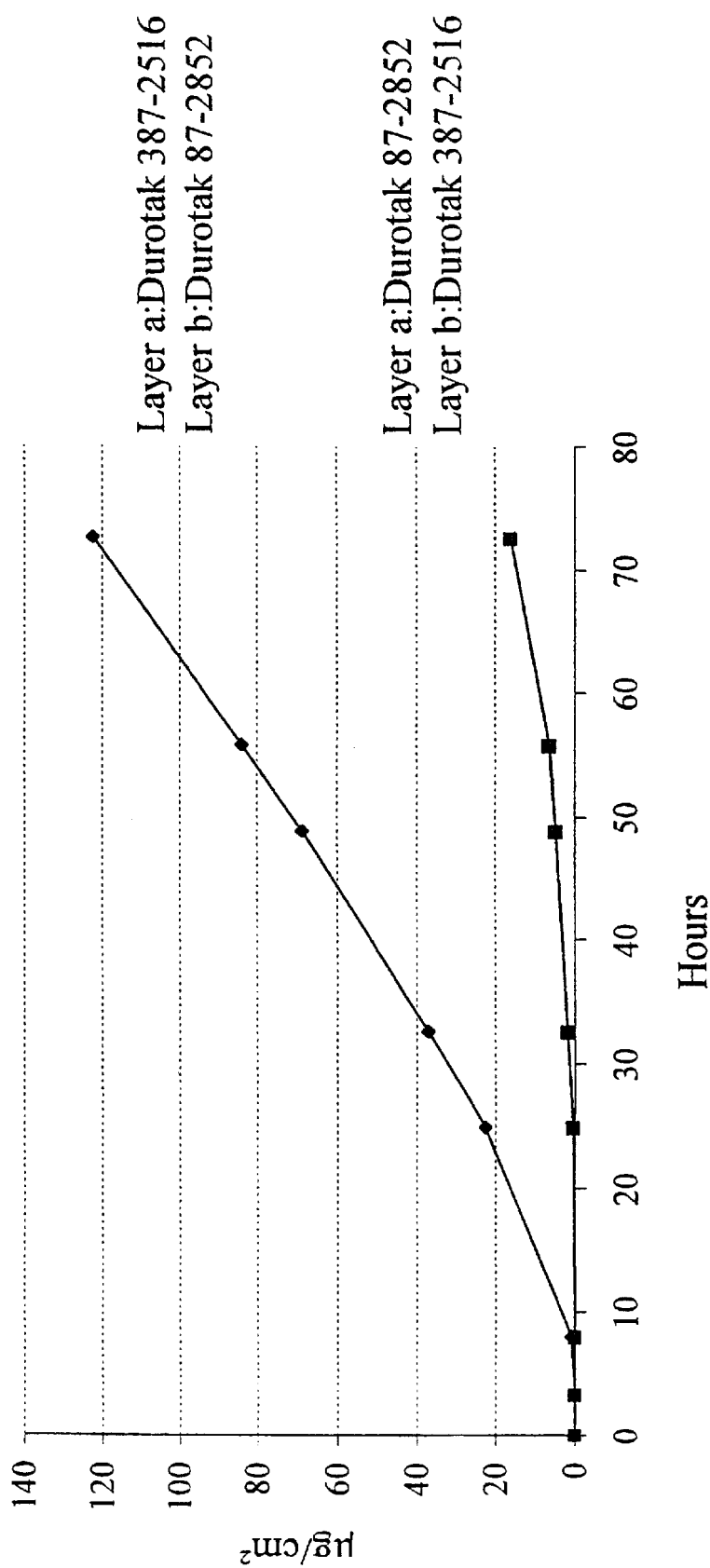
FIG. 27 is a diagram showing in vitro skin permeation of tolterodine base from multilaminate patches according to Example 31.

In vitro skin permeation study of the transdermal drug delivery Systems 12 and 13 according to Example 28 and 29 (FIG. 27).

In vitro skin permeation of tolterodine base through dermatomed pigskin was investigated using Franz diffusion cells. Samples were withdrawn periodically up to 48 hours. The amount of tolterodine base in the samples was determined by HPLC.

The cumulative amount of tolterodine base in the receptor solution versus time is shown in FIG. 27. The results show that it is possible to vary the release profile by chancing the polymers in the multilaminate patch.

Example 32

System 14 (drug-in-adhesive, silicone)

4.5 g of tolterodine base was dissolved in 46 g PSA-9839. The drug gel was coated onto a polyester release liner (Scotchpak 1022) by using the coating equipment. The laminate was dried at 50° C., for 10 min. The dry coat weight was approximately 150 g/m$^2$. A backing membrane (Scotchpak 1109) was laminated onto the dried drug gel. The sheets were cut into patches and stores at 2–8° C. until use (packed in Barex pouches). The theoretically concentration (not analysed) of tolterodine base in the patches was 1.5 mg/cm$^2$.

Example 33

Figure 28:
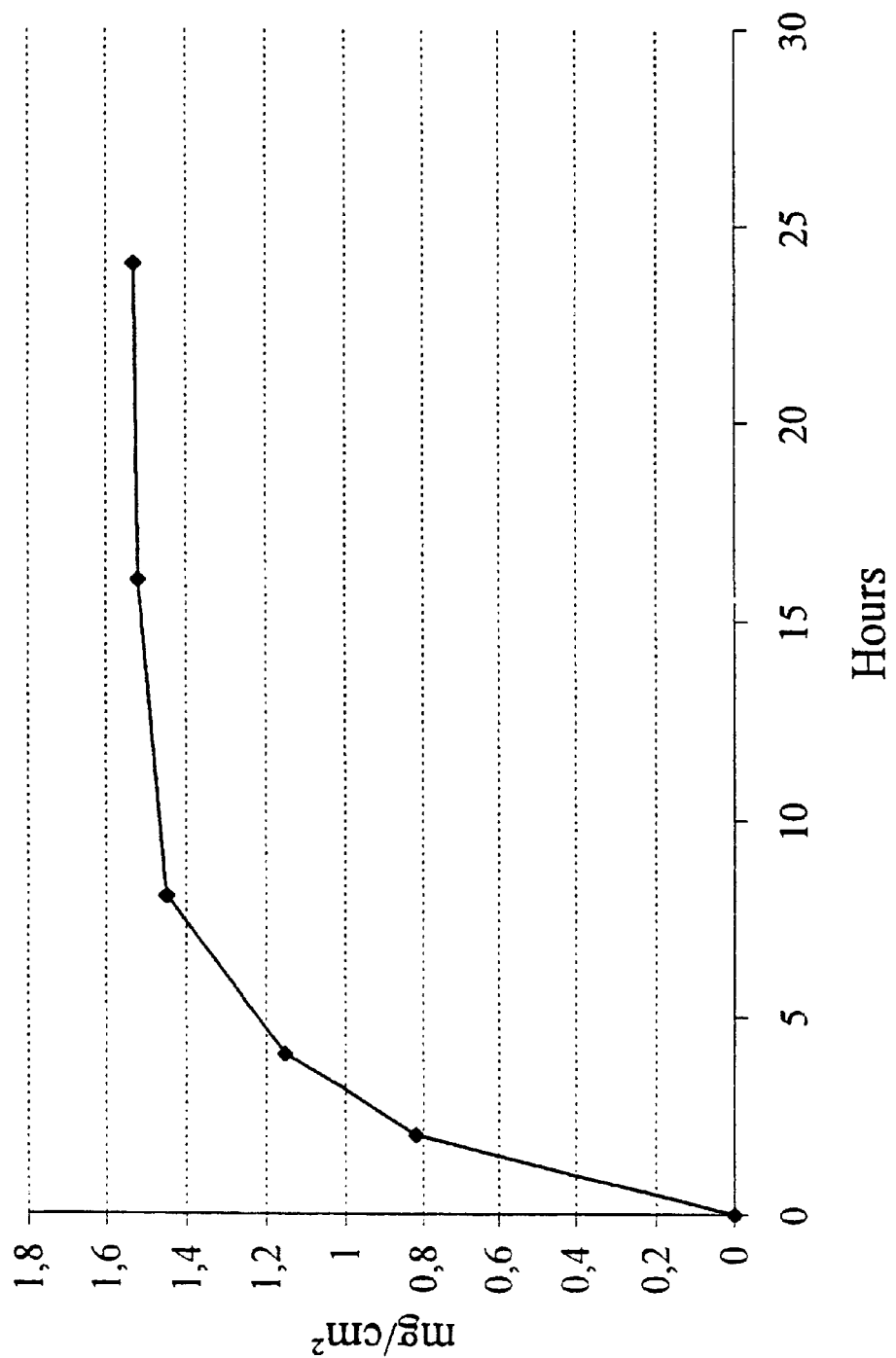
FIG. 28 is a diagram showing in Vitro dissolution of tolterodine base from a silicone adhesive according to Example 33.

In vitro dissolution study of the transdermal delivery System 14 according to Example 32 (FIG. 28).

Patches of 10 cm$^2$ were applied to the disk assembly, using a suitable adhesive, with the release surface facing up. Samples were withdrawn periodically up to 24 hours. The amount of tolterodine base in the samples was determined by HPLC and the amount of tolterodine base released from the patches was expressed in mg tolterodine base per cm$^2$. It can be seen from the results that the entire tolterodine base was released after 8 hours.

Example 34

Figure 29:
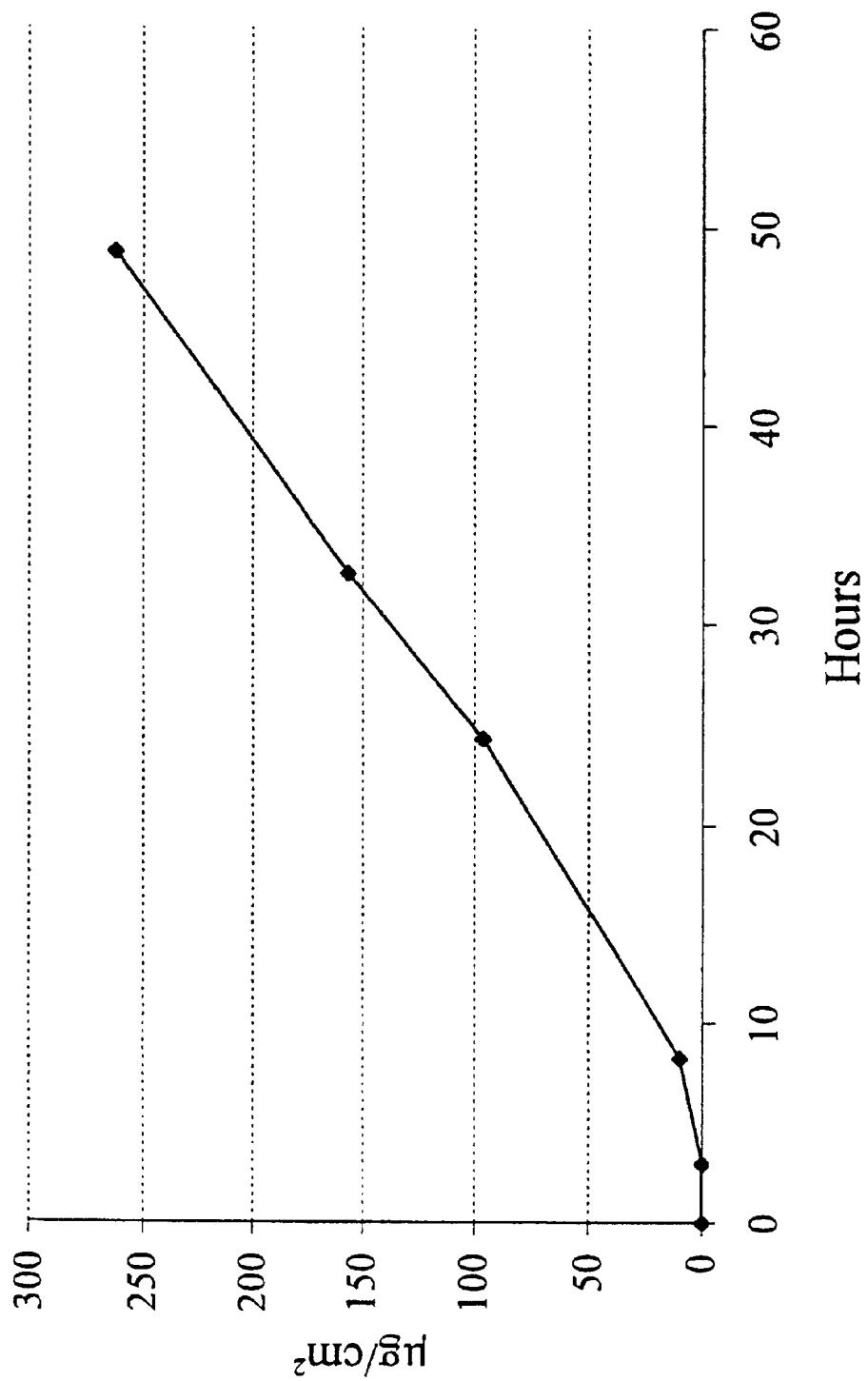
FIG. 29 is a diagram showing in vitro skin permeation of tolterodine base from a silicone adhesive according to Example 34.

In vitro skin permeation study of the transdermal drug delivery System 14 according to Example 32 (FIG. 29).

In vitro skin permeation of tolterodine base through dermatomed pigskin was investigated using Franz diffusion cells. Samples were withdrawn periodically up to 48 hours. The amount of tolterodine base in the samples was determined by HPLC.

The cumulative amount of tolterodine base in the receptor solution versus time is shown in FIG. 29. The obtained flux was 7 µg/cm$^2$/h and the amount of tolterodine base that permeated the skin was about 17% (calculated from the theoretically calculated amount of tolterodine base in the patch).

Example 35

System 15 (drug-in-adhesive, acryate non-occlusive backing membrane)

1 g of tolterodine base was dissolved in 20 g Durotak 387-2516. The drug gel was coated onto a polyester release liner (FL 2000-696029/3) by using the coating equipment. The laminate was dried at 80° C. for 10 min. The dry coat weight was approximately 115 g/m$^2$. A non-occlusive backing membrane ("Emflon 11" 0.2 µm PVDF) was laminated onto the dried drug gel. The sheets were cut into patches and stored at 2–8° C. until use (packed in Barex pouches). The theoretically calculated concentration (not analysed) of tolterodine base in the patches was 1.0 mg/cm$^2$.

Example 36

Figure 30:
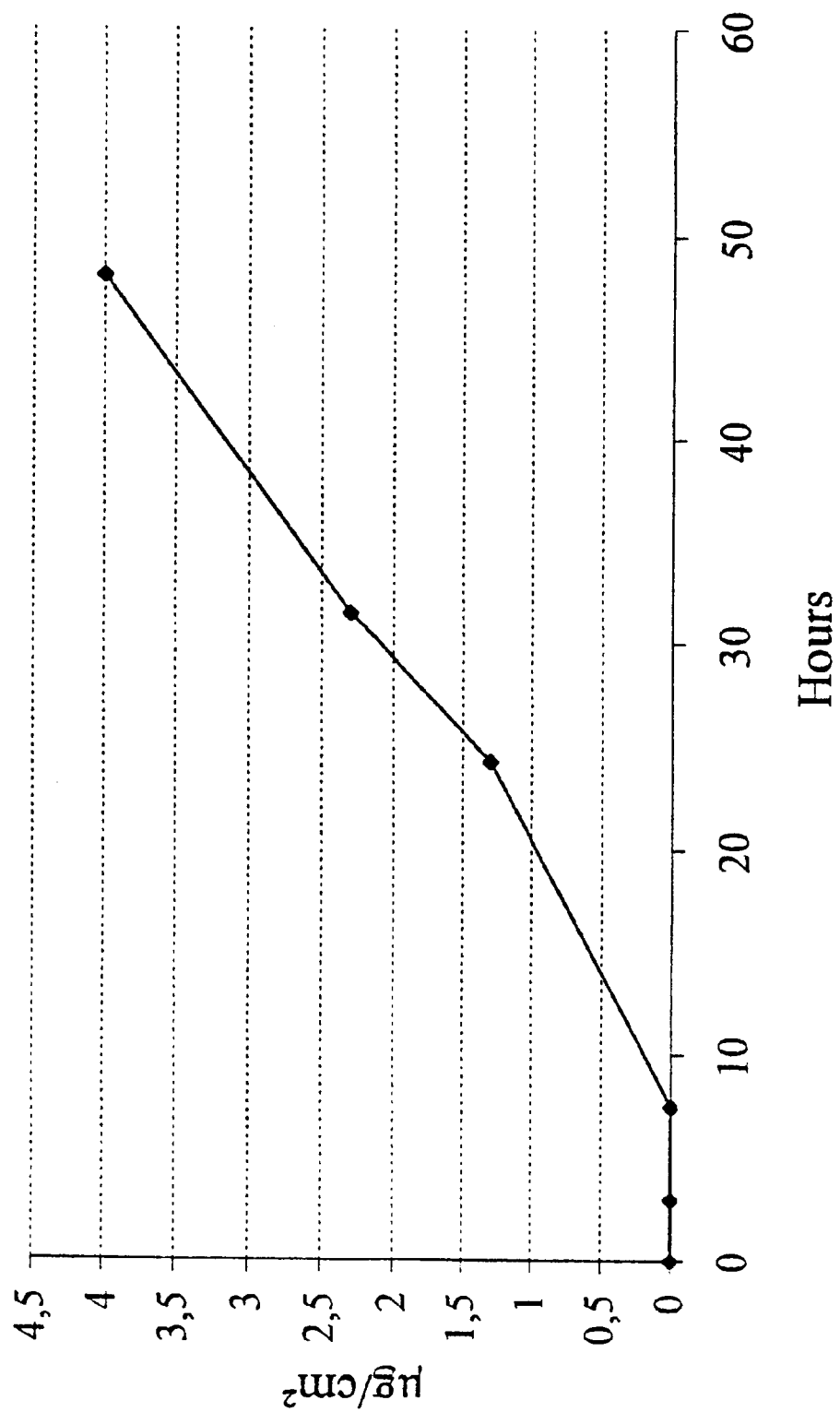
FIG. 30 is a diagram showing in vitro skin permeation of tolterodine base from patches where a non-occlusive membrane has been used as a backing according to Example 36.

In vitro skin permeation study of the transdermal drug delivery System 15 according to Example 35 (FIG. 30).

In vitro skin permeation of tolterodine base through dermatomed pigskin was investigated using Franz diffusion cells. Samples were withdrawn periodically up to 48 hours. The amount of tolterodine base in the samples was determined by BPLC.

The cumulative amount of tolterodine base in the receptor solution versus time is shown in FIG. 30. The obtained flux was 0.1 µg/cm$^2$/h and the amount of tolterodine base that permeated the skin was about 0.4% (calculated from the theoretically calculated amount of tolterodine base in the patch). That is, only a very small amount of tolterodine permeates the skin compared to when an occlusive backing membrane is used.

Example 37

System 16 (Reservoir patch)

7 g tolterodine base was dissolved in 65 g ethanol whereafter 65 g propylene glycol and 3.5 g methyl laurate were added. 750 µl was filled in each reservoir patch using the reservoir machine. As backing membrane was used Scotchpak 1012 and as rate controlling membrane was used CoTran 9702 - 9% Vinyl Acetate). No adhesive was applied to the reservoir patch. The concentration of tolterodine base in the reservoir patches was 1.4 mg/cm$^2$.

Example 38

Figure 31:
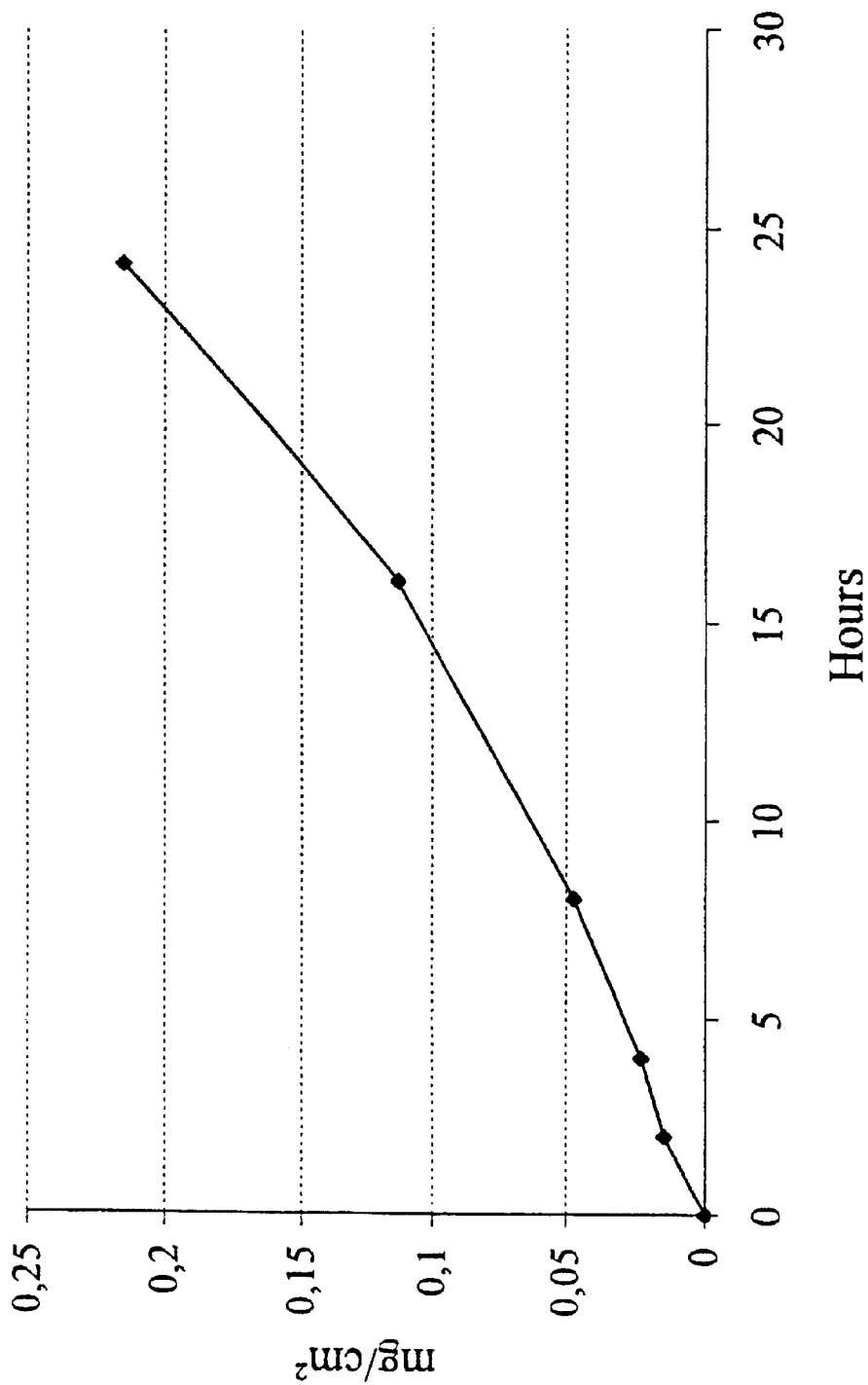
FIG. 31 is a diagram showing in vitro dissolution of tolterodine base from a reservoir patch according to Example 38.

In vitro dissolution study of the transdermal drug delivery System 16 according to Example 37 (FIG. 31).

Reservoir patches of 30 cm$^2$ were applied to the convex screen by means of a 50 cm$^2$ placebo drug-in-adhesive patch made of Durotak 387-2287, with the release surface facing up. Samples were withdrawn periodically up to 24 hours. The amount of tolterodine base in the samples was determined by HPLC and the amount of tolterodine base released from the patches was expressed in mg tolterodine base per cm$^2$. The result show that 15% of the tolterodine base was released after 24 hours.

Example 39

Figure 32:
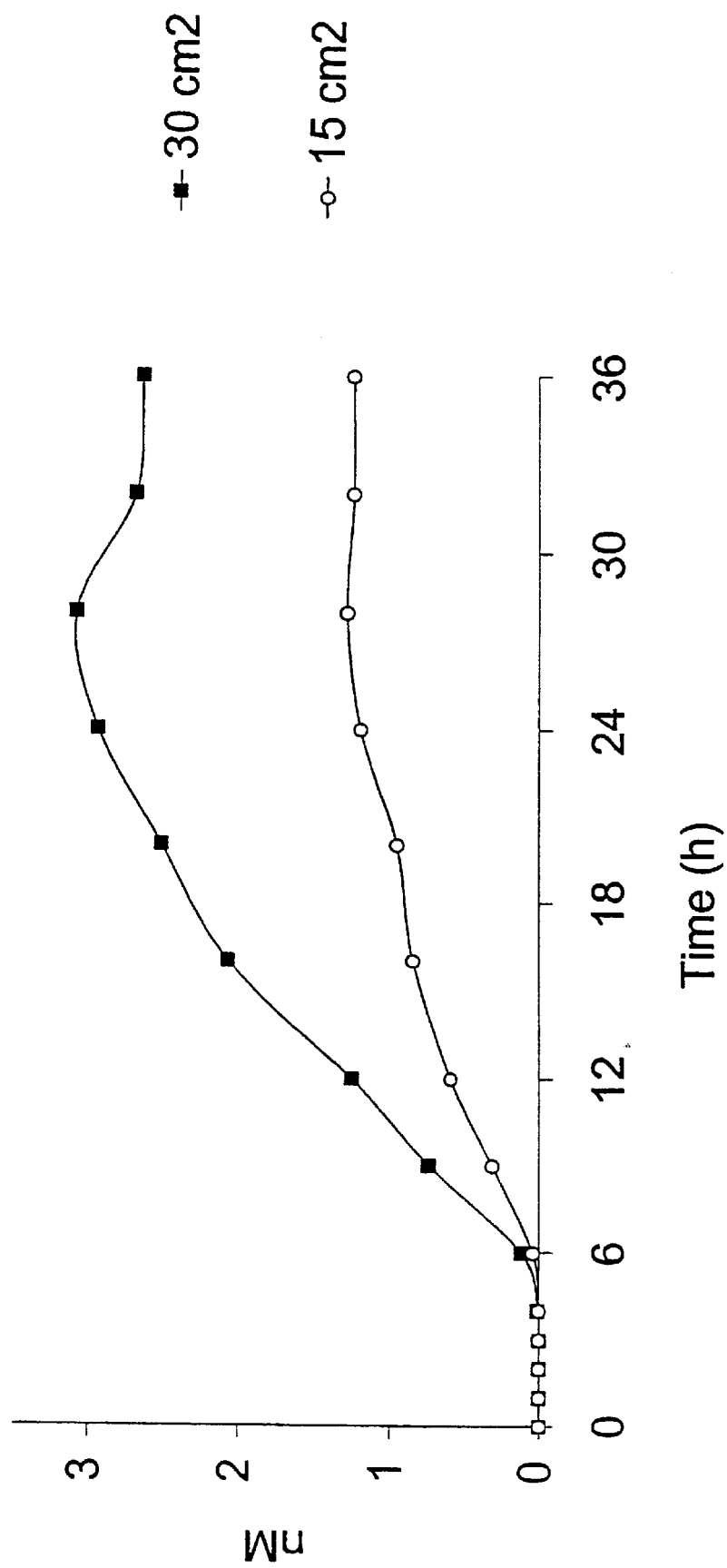
FIG. 32 is a diagram showing in vitro data from a bioavailability study according to Example 39.

Bioavailability study of transdermal patches of tolterodine base (1.79 mg/cm$^2$). An open single-sequence, dose-escalation study in 8 healthy volunteers (FIG. 32).

The clinical study was performed at Quintiles Phase I Clinic, Uppsala, Sweden. Each subject started with a 15 cm$^2$ patch. After a two-week washout period the subjects continued with a 30 cm$^2$ patch. The patches were applied on the dorsal side of the upper arm for 36 hours whereafter the residual amount of tolterodine base in the patch was analysed. Blood sampling for determination of tolterodine base and metabolites were drawn pre-dose and during the 36 hours the patches were applied to the subjects. Results from the blood sampling are shown in FIG. 32. It was seen that an apparent steady state was reached approximately 24 hours after application.

Results from the analysis of the residual amount of tolterodine base in the patches showed that about 4.8 mg, tolterodine base from the 15 cm$^2$ patch and about 10.6 mg tolterodine base from the 30 cm$^2$ patch (corresponding to 7.2 and 15.9 mg tolterodine tartrate respectively) was released from the patches and thus permeated into the skin.

A iontophoretic type device may be manufactured essentially according to embodiments disclosed in e.g. Parminder Sinch et al, "Iontophoresis in Drug Delivery: Basic Principles and Applications", Critical Reviews in Therapeutic Drug Carrier Systems, 1994; 11 (2&3):161–213. The administration of tolterodine or an acid salt thereof is not disclosed in this reference. Anyhow it lies within the present invention to modify, using the disclosure in the present application, the embodiments according to said reference to become suitable for the administration of tolterodine.

The above examples show that it is possible to administer tolterodine and to control its release rate using all known types of devices for transdermal drug administration.

Some prodrug type derivatives of tolterodine, DD 01, or other metabolites of tolterodine can be used according to the present invention for obtaining the desirable effect. Other salts than the tartrate could be used as it is known that other anions than tartrate may generate ion-pairs with more favourable skin permeation rates.

Various carriers and vehicles for tolterodine may be used in the transdermal administration. One such carrier is cyclodextrine, especially β-cyclodextrine. Tolterodine can be bound in the cavities of cyclodextrines to form so called inclusion complexes. Binding tolterodine to a cyclodextrine leads either to increased delivery rate or to decreased delivery rate depending on the tolterodine-cyclodextrine ratio.

The data in FIGS. 10–13 show that an apparent 0-order delivery of tolterodine through the skin takes place from about 5 to 48 hours. During, that period, only about 10% of the loaded amount of drug in the devices is exhausted and thus this 0-order delivery rate can be maintained at least up to 7 days. Such a once-weekly patch will greatly improve patient compliance, which is important as elderly patients often use tolterodine.

It might be desirable to use higher dosages of drug during the day or night, depending on the time when the overactive bladder is more troublesome. It is within the present invention to administer tolterodine in such a way that a therapeutically effective systemic level of tolterodine prevails to a higher extent during the day or the night. The above object is achievable by applying the transdermal device at the appropriate time during day or night in combination with designing the device with the appropriate release profile. The same rules for a device designed to deliver tolterodine to a lower extent during the day or the night.

Dosage

The required input rate (Ro) of tolterodine from a transdermal formulation can be exemplified by the following estimation for a poor metabolizer. The systemic clearance (CL) is about 10L/h and the average serum concentration (C) after tolterodine 2 mg bid is about 10 μg/L. (Brynne et al. Clin Pharmacol. Ther. 1998)). Thus, Ro=CL·C=100 μg/h=2.4 mg/24 h=2 μg/h/cm² (assuming the practically maximum patch area to be 50 cm²). Required minimum patch area will be about 3 cm² (assuming a practically maximum flux rate of 35 μg/h/cm²). These estimations show the feasibility of producing transdermal formulations that may be clinically useful.

Based on the pharmacokinetic properties of tolterodine in the population to be treated, the clinical efficacy profile, the age and body weight range to be covered (including the children indication) and the properties of the patch formulation required, patch areas are mainly expected to be in the range 3–50 cm². Patches will be constructed for release rates ranging from 0.2–35 μg/h/cm². DD 01 will also be used as an alternative as the active ingredient in transdermal formulations.

A useful device for transdermal administration of tolterodine should have an hourly flux rate of tolterodine from about 0.1 μg/h/cm² to about 100 μg/h/cm², preferably from about 0.2 μg/h/cm² to about 35 μg/h/cm² and an area of from about 2 cm² to about 100 cm², preferably from about 5 cm² to about 30 cm².

The above release rates implicit that a device for transdermal delivery of tolterodine should have a loading of tolterodine from about 0.1 mg/cm² to about 5 μg/cm².

It should also be contemplated that a device for transdermal delivery during 2 or more days would further facilitate the use of the transdermal formulation. It is possible to design a device delivers tolterodine for a predefined period of time, preferably 12, 24 or 48 hours, or even up to 7 or 14 days.

When tolterodine is administered in a transdermal device the latter should preferably be occlusive, which means that the device does not permit water to migrate outwardly from the skin area covered by the device or at least with a lower rate than the rate of the skins ordinary transepidermal water loss. Thereby the hydration of the skin is increased which favours the penetration of tolterodine through the skin.

For convenience and/or in order to achieve a more rapid increase in plasma level it is possible to design a set of formulations of tolterodine, optionally encompassing salts, prodrugs and metabolites thereof, which comprises at least one device for transdermal delivery and at least one formulation for oral, sublingual, buccal, nasal, pulmonary, rectal and/or other transmucosal administration.

In all the different embodiments of the present invention tolterodine may be present in just one of its above-presented forms or as mixture of two or more forms.

What is claimed is:

1. Device for transdermal administration, comprising
   at least one compound having a therapeutic effect against an overactive bladder in a living body which is selected from the group consisting of (R)-tolterodine or the racemate thereof, salts thereof, prodrugs thereof, and metabolites thereof, and
   a transdermal administration device selected from the group consisting of a reservoir, a matrix, a drug-in-adhesive, a multi-laminate, a polymer-system with no foils, a iontophoretic device, and combinations thereof, an electroporation, an electroosmosis, an electroincorporation and a jet injection device which contains said compound and which has an hourly flux rate of said at least one compound from about 0.1 μg/h/cm² to about 100 μg/h/cm².

2. Device for transdermal administration according to claim 1, characterized in that tolterodine essentially is in its R-isomeric form.

3. Device for transdermal administration according to claim 1, characterized in that tolterodine essentially is in racemic form.

4. Device for transdermal administration according to claim 1, characterized in that the (R)-tolterodine is the tolterodine metabolite (R)-N,N-diisopropyl-3-(2-hydroxy-5-hydroxymethylphenyl)-3-phenylpropanamine.

5. Device for transdermal administration according to claim 1 characterized in that it has a loading of tolterodine from about 0.1 mg/cm² to about 5 mg/cm².

6. Device for transdermal administration according to claim 1, characterized in that it has an area of from about 2 cm² to about 100 cm².

7. Device for transdermal administration according to claim 1, characterized in that it delivers said at least one compound for a predefined period of time.

8. Device for transdermal administration, comprising
   at least one compound having a therapeutic effect against an overactive bladder in a living body which is selected from the group consisting of (R)-tolterodine or the racemate thereof, salts thereof, prodrugs thereof, and metabolites thereof, wherein said at least one compound is present in a complex with cyclodextrin; and a transdermal administration device selected from the group consisting of a reservoir, a matrix, a drug-in-adhesive, a multi-laminate, a polymer-system with no foils, a iontophoretic device, and combinations thereof, an electroporation, an electroosmosis, an electroincorporation and a jet injection device which contains said compound and which has an hourly flux rate of said at least one compound from about 0.1 µg/h/cm² to about 100 µg/h/cm².

9. Device according to claim 1, characterized in that it has a release profile being, such that it, when applied on the skin at the appropriate time during day or night, administers tolterodine in such a way that a therapeutically effective systemic level of tolterodine prevails mainly during such periods of time during day and night when an effect against overactive bladder is most desirable.

10. Device according to claim 1, characterized in that it further comprises a substance enhancing transdermal penetration.

11. Device according to claim 1, characterized in that it further comprises a substance reducing irritant reactions.

12. Device according to claim 1, characterized in that it is occlusive.

13. Method for achieving an effect against an overactive bladder in a living body which comprises transdermally administering with a transdermal administration device of claim 1 at least one compound selected from the group consisting of (R)-tolterodine or the racemate thereof, salts thereof, prodrugs thereof, and metabolites thereof.

14. Method according to claim 13, characterized in that tolterodine essentially is in its R-isomeric form.

15. Method according to claim 13, characterized in that tolterodine essentially is in racemic form.

16. Method according to claim 13, characterized in that the trandsdermally administered compound comprises the (R)-tolterodine metabolite (R)-N,N-diisopropyl-3-(2-hydroxy-5-hydroxymethylphenyl)-3-phenylpropanamine.

17. Method according to claim 13, wherein in the treatment is achieved through systemic effect of the transdermally administered compound.

18. Method for achieving an effect against an overactive bladder and/or symptoms associated with this condition in a living body which comprises transdermally administering with a transdermal administration device of claim 1 at least one compound selected from the group consisting of (R)-tolterodine or the racemate thereof, salts thereof, prodrugs thereof, and metabolites thereof.

19. Method according to claim 13, characterized in that tolterodine is administered in such a way that a therapeutically effective systemic level of tolterodine prevails mainly during those periods of time during day and night when an effect against overactive bladder is most desirable.

20. Method according to claim 13, characterized in that tolterodine is administered in such a way that a less than therapeutically effective systemic level of tolterodine prevails mainly during those periods of time during day and night when an effect against overactive bladder is less desirable.

21. Device according to claim 1, further comprising at least one pharmaceutically acceptable carrier.

22. Device according to claim 4, further comprising tolterodine.

23. Device according to claim 1, characterized in that the device is a drug-in-adhesive or reservoir device.

24. Device according to claim 1, characterized in that the device is a combination of a drug-in-adhesive device and a reservoir device.

25. Device for transdermal administration according to claim 1, characterized in that it has an hourly flux rate of said at least one compound from about 0.2µg/h/cm² to about 35 µg/h/cm².

26. Device for transdermal administration according to claim 6, characterized in that it has an area of from about 5 cm² to about 30 cm².

27. Device for transdermal administration according to claim 7, characterized in that it delivers said at least one compound for 12, 24 or 48 hours.

28. Device for transdermal administration according to claim 7, characterized in that it delivers said at least one compound for up to 7 or 14 days.

29. Device according to claim 8, characterized in the cyclodextrin is β-cyclodextrin.

30. Method according to claim 13, further comprising at least one pharmaceutically acceptable carrier.

31. Method according to claim 16, characterized in that the (R)-tolterodine metabolite, (R)-N,N-diisopropyl-3-(2-hydroxy-5-hydroxymethylphenyl)-3-phenylpropanamine, is administered together with tolterodine.

32. Method according to claim 13, wherein the transdermal administration is carried out using a drug-in-adhesive or reservoir device.

33. Method according to claim 13, wherein the transdermal administration is carried out using a combination of a drug-in-adhesive device and a reservoir device.

34. Method according to claim 18 characterized in that said at least compound is administered together with at least one pharmaceutically acceptable carrier.

35. Method according to claim 18 further comprising oral, sublingual, buccal, nasal, pulmonary, rectal and/or other transdermal administration of a compound comprising tolterodine, salts thereof, prodrugs thereof and metabolites thereof, and optionally together with pharmaceutically acceptable carrier(s).

36. Method according to claim 5, characterized in that said oral, sublingual, buccal, nasal, pulmonary, rectal and/or other transdermal administered compound is administered together with at least one pharmaceutically acceptable carrier.

* * * * *